(12) United States Patent
Scheuing et al.

(10) Patent No.: US 9,474,269 B2
(45) Date of Patent: Oct. 25, 2016

(54) AQUEOUS COMPOSITIONS COMPRISING ASSOCIATIVE POLYELECTROLYTE COMPLEXES (PEC)

(75) Inventors: David R. Scheuing, Pleasanton, CA (US); William L. Smith, Pleasanton, CA (US); Michael Kinsinger, Pleasanton, CA (US); Jared Heymann, Pleasanton, CA (US)

(73) Assignee: The Clorox Company, Oakland, CA (US)

( * ) Notice: Subject to any disclaimer, the term of this patent is extended or adjusted under 35 U.S.C. 154(b) by 341 days.

(21) Appl. No.: 13/046,385

(22) Filed: Mar. 11, 2011

(65) Prior Publication Data
US 2011/0236450 A1 Sep. 29, 2011

Related U.S. Application Data

(63) Continuation-in-part of application No. 12/749,288, filed on Mar. 29, 2010, now abandoned.

(51) Int. Cl.
*A01N 33/12* (2006.01)
*A01N 59/00* (2006.01)
(Continued)

(52) U.S. Cl.
CPC ............... *A01N 33/12* (2013.01); *A01N 59/00* (2013.01); *A01N 59/16* (2013.01); *A61L 15/10* (2013.01); *A61L 15/46* (2013.01)

(58) Field of Classification Search
None
See application file for complete search history.

(56) References Cited

U.S. PATENT DOCUMENTS

| 3,896,056 A | 7/1975 | Benjamin et al. |
| 3,950,260 A | 4/1976 | Eldib |

(Continued)

FOREIGN PATENT DOCUMENTS

| EP | 0342997 B2 | 5/1989 |
| WO | WO 01/23511 A1 | 4/2001 |

(Continued)

OTHER PUBLICATIONS

Zezin et al., A New Class of Complex Water-soluble polyelectrolytes, Russian Chemical Reviews, 51,9,1982, 833-855.*

(Continued)

*Primary Examiner* — Francisco Tschen
(74) *Attorney, Agent, or Firm* — Alok Goel

(57) ABSTRACT

The present invention relates to aqueous compositions of associative polyelectrolyte complexes (PECs), optionally containing surfactants, biocidal agents and/or oxidants, which can provide a cleaning benefit and surface protection to treated articles including reduced soiling tendency, reduced cleaning effort and improved soil repellancy, as well as providing bacteriostatic properties to treated surfaces that thereby gain resistance to water, environmental exposure and microbial challenge. Treatment means and compositions are provided that employ associative polyelectrolyte complexes formed by combining a water soluble cationic first polyelectrolyte with a water soluble second polyelectrolyte bearing groups of opposite charge to the first polyelectrolyte under suitable mixing conditions and at least one oxidant selected from the group: alkaline metal salts and/or alkaline earth metal salts of hypochlorous acid, hypochlorous acid, solubilized chlorine, any source of free chlorine, acidic sodium chlorite, active chlorine generating compound and any combinations or mixtures thereof. Also provided are means to form stable associative polyelectrolyte complexes with at least one oxidant in aqueous solutions having R values from about 0.10 to 20.

17 Claims, 8 Drawing Sheets

(51) Int. Cl.
  *A01N 59/16* (2006.01)
  *A61L 15/10* (2006.01)
  *A61L 15/46* (2006.01)

(56) References Cited

U.S. PATENT DOCUMENTS

| | | | |
|---|---|---|---|
| 4,147,649 A | 4/1979 | Arnau et al. | |
| 4,301,067 A | 11/1981 | Koshugi | |
| 4,501,834 A | 2/1985 | Su | |
| 4,501,835 A | 2/1985 | Berke | |
| 4,681,696 A | 7/1987 | Bruegge | |
| 4,710,374 A | 12/1987 | Grollier et al. | |
| 4,999,386 A | 3/1991 | Oakes et al. | |
| 5,049,383 A | 9/1991 | Huth et al. | |
| 5,158,766 A | 10/1992 | Greenwald et al. | |
| 5,578,598 A | 11/1996 | Abe et al. | |
| 5,700,559 A | 12/1997 | Sheu et al. | |
| 5,858,938 A | 1/1999 | Glen, Jr. et al. | |
| 5,874,524 A | 2/1999 | Pakusch et al. | |
| 6,017,561 A | 1/2000 | Zhou et al. | |
| 6,028,043 A | 2/2000 | Glen, Jr. et al. | |
| 6,221,399 B1 | 4/2001 | Rolfes et al. | |
| 6,270,754 B1 | 8/2001 | Zhou et al. | |
| 6,638,918 B2 | 10/2003 | Davison et al. | |
| 6,703,358 B1 | 3/2004 | Aubay et al. | |
| 6,743,775 B2 | 6/2004 | Santar et al. | |
| 6,838,078 B2 | 1/2005 | Wang et al. | |
| 6,849,586 B2 | 2/2005 | Avery et al. | |
| 6,887,564 B2 | 5/2005 | Gagliardini et al. | |
| 6,939,554 B2 | 9/2005 | McDonald et al. | |
| 7,018,709 B2 | 3/2006 | Stevenson et al. | |
| 7,141,617 B2 | 11/2006 | Gratson et al. | |
| 7,288,514 B2 | 10/2007 | Scheuing et al. | |
| 7,511,008 B2 | 3/2009 | Scheuing et al. | |
| 8,728,454 B1 | 5/2014 | Scheuing | |
| 8,728,530 B1 | 5/2014 | Scheuing | |
| 8,765,114 B2 | 7/2014 | Scheuing | |
| 8,883,705 B2 | 11/2014 | Scheuing | |
| 8,883,706 B2 | 11/2014 | Scheuing | |
| 8,933,010 B2 | 1/2015 | Scheuing | |
| 8,975,220 B1 | 3/2015 | Kaur | |
| 8,993,505 B2 | 3/2015 | Scheuing | |
| 9,012,389 B2 | 4/2015 | Scheuing | |
| 9,045,719 B1 | 6/2015 | Kaur | |
| 2001/0003221 A1 | 6/2001 | Akbarian et al. | |
| 2001/0056058 A1 | 12/2001 | Panandiker et al. | |
| 2002/0010105 A1 | 1/2002 | Bacon et al. | |
| 2002/0010124 A1 | 1/2002 | Creeth | |
| 2002/0019328 A1 | 2/2002 | Schroeder | |
| 2002/0049149 A1 | 4/2002 | Durbut et al. | |
| 2002/0082181 A1* | 6/2002 | Humphrey et al. | 510/305 |
| 2002/0151454 A1* | 10/2002 | Kischkel et al. | 510/466 |
| 2002/0169097 A1 | 11/2002 | Kasturi et al. | |
| 2003/0059398 A1 | 3/2003 | Ranger et al. | |
| 2003/0064905 A1 | 4/2003 | Eldib | |
| 2003/0114342 A1 | 6/2003 | Hall | |
| 2003/0147826 A1 | 8/2003 | Anthony et al. | |
| 2003/0176306 A1 | 9/2003 | McKechnie | |
| 2003/0183253 A1 | 10/2003 | Cornelius | |
| 2003/0216281 A1 | 11/2003 | DeLeo et al. | |
| 2003/0228992 A1 | 12/2003 | Smets et al. | |
| 2004/0013638 A1 | 1/2004 | Aubay et al. | |
| 2004/0052748 A1 | 3/2004 | Vondruska | |
| 2004/0103483 A1 | 6/2004 | Delplancke et al. | |
| 2004/0138084 A1 | 7/2004 | Gohl | |
| 2004/0149315 A1 | 8/2004 | Kim | |
| 2004/0152617 A1 | 8/2004 | Murphy et al. | |
| 2004/0170587 A1 | 9/2004 | Vondruska | |
| 2004/0194800 A1 | 10/2004 | Chang et al. | |
| 2004/0221873 A1 | 11/2004 | Rusciolelli | |
| 2005/0008534 A1 | 1/2005 | Hodge et al. | |
| 2005/0009971 A1 | 1/2005 | Hodge et al. | |
| 2005/0013794 A1 | 1/2005 | Hodge et al. | |
| 2005/0014670 A1 | 1/2005 | Hodge et al. | |
| 2005/0026801 A1 | 2/2005 | Broeckx et al. | |
| 2005/0096239 A1 | 5/2005 | Barnabas et al. | |
| 2005/0154361 A1 | 7/2005 | Sabesan | |
| 2005/0159321 A1 | 7/2005 | Cusack et al. | |
| 2005/0182021 A1 | 8/2005 | Nichols et al. | |
| 2005/0204477 A1 | 9/2005 | Casella | |
| 2005/0233938 A1 | 10/2005 | Delplancke et al. | |
| 2006/0035805 A1 | 2/2006 | Penninger | |
| 2006/0035807 A1 | 2/2006 | Kasturi | |
| 2006/0058214 A1 | 3/2006 | Zhang et al. | |
| 2006/0073994 A1* | 4/2006 | Hage et al. | 510/101 |
| 2006/0074005 A1 | 4/2006 | Kischkel et al. | |
| 2006/0196834 A1* | 9/2006 | Nichols | B01D 21/01 210/702 |
| 2006/0275337 A1* | 12/2006 | Cohen Stuart et al. | 424/423 |
| 2006/0276371 A1 | 12/2006 | Schreiner et al. | |
| 2007/0054828 A1 | 3/2007 | Gentschev | |
| 2007/0243237 A1* | 10/2007 | Khaled | A01N 25/10 424/443 |
| 2007/0259800 A1 | 11/2007 | Boutique et al. | |
| 2007/0293414 A1 | 12/2007 | Panandiker et al. | |
| 2008/0108537 A1 | 5/2008 | Rees | |
| 2008/0148491 A1 | 6/2008 | van Buskirk | |
| 2008/0206293 A1* | 8/2008 | Toreki | A61L 15/46 424/404 |
| 2010/0237282 A1 | 9/2010 | Komatsu et al. | |
| 2010/0316715 A1 | 12/2010 | Andersson | |
| 2011/0236450 A1 | 9/2011 | Scheuing | |
| 2011/0236582 A1 | 9/2011 | Scheuing | |
| 2013/0165525 A1 | 6/2013 | Scheuing | |
| 2013/0165572 A1 | 6/2013 | Scheuing | |
| 2013/0216293 A1 | 8/2013 | Garner | |
| 2013/0216631 A1 | 8/2013 | Garner et al. | |
| 2013/0217610 A1 | 8/2013 | Scheuing | |
| 2013/0273174 A1 | 10/2013 | Scheuing | |
| 2014/0116917 A1 | 5/2014 | Scheuing | |
| 2014/0116918 A1 | 5/2014 | Scheuing | |
| 2014/0120054 A1 | 5/2014 | Scheuing | |
| 2014/0120055 A1 | 5/2014 | Scheuing | |
| 2014/0120056 A1 | 5/2014 | Scheuing et al. | |
| 2014/0121281 A1 | 5/2014 | Scheuing | |
| 2014/0200300 A1 | 7/2014 | Scheuing | |
| 2014/0212511 A1 | 7/2014 | Scheuing | |
| 2014/0296126 A1 | 10/2014 | Scheuing | |
| 2015/0038392 A1 | 2/2015 | Scheuing | |
| 2015/0264922 A1 | 9/2015 | Scheuing | |

FOREIGN PATENT DOCUMENTS

| | | | |
|---|---|---|---|
| WO | WO 03/068843 A1 | 8/2003 | |
| WO | WO 2004/041986 A1 | 5/2004 | |
| WO | WO 2005/044967 A2 | 5/2005 | |
| WO | WO 2005/072712 A2 | 8/2005 | |
| WO | WO 2005/092273 A2 | 10/2005 | |
| WO | 2007009917 A1 | 1/2007 | |
| WO | 2007/022235 A1 | 2/2007 | |
| WO | WO 2007/022235 A1 | 2/2007 | |
| WO | 2008/134212 A1 | 11/2008 | |

OTHER PUBLICATIONS

Stuart et al. Colloids & Surfaces 242 (2004) 167-174.
Stuart et al. Langmuir 2004 (20) 1073-1084.
Tiller European Coatings Journal—BIOCIDES—12 (06) 28-32.
Buchhammer et al. Colloids & Surfaces 122 (1997) 1-12.
Buchhammer et al. Colloids & Surfaces 137 (1998) 45-56.
Buchhammer et al. Colloids & Surfaces 140 (1998) 377-384.
Buchhammer et al. Colloids & Surfaces 218 (2003) 151-159.
Buchhammer et al. Colloid Polym Sci 278 (2000) 841-847.
Chua (Wal-Mart to Sell Only Concentrated Laundry Detergent Category by 2008, Jasmin Malik Chua, Oct. 1, 2007, http://www.treehugger.com/corporate-responsibility/wal-mart-to-sell-only-concentrated-laundry-detergent-category-by-2008.html, Retrieved Jun. 12, 2013).
Dautzenberg (Dautzenberg, H., Polyelectrolyte Complex Formation in Highly Aggregating Systems, 1, Effect of Salt: Polyelectrolyte Complex Formation in the Presence of NaCl, Macromolecules 1997, 30, 7810-7815).

(56) References Cited

OTHER PUBLICATIONS

Zintchenko et al., Polyelectrolyte Complex Formation with Double Hydrophilic Block Polyelectrolytes: Effects of the Amount and Length of the Neutral Block, Langmuir 2002, 18, 1386-1393.
Kitchen Clean-Up, EC 1552-E, Oregon State University Extension Service, Published Sep. 2002.
US Non-Final Rejection, dated Jul. 12, 2013, from U.S. Appl. No. 13/772,674, filed Feb. 21, 2013.
US Non-Final Rejection, dated Oct. 31, 2013, from U.S. Appl. No. 13/772,674, filed Feb. 21, 2013.
US Non-Final Rejection, dated Aug. 8, 2014, from U.S. Appl. No. 13/772,674, filed Feb. 21, 2013.
US Non-Final Rejection, dated Aug. 4, 2014, from U.S. Appl. No. 14/227,272, filed Mar. 27, 2014.
US Non-Final Rejection, dated Aug. 13, 2014, from U.S. Appl. No. 14/277,363, filed Mar. 27, 2014.
US Non-Final Rejection, dated Sep. 30, 2014, from U.S. Appl. No. 14/456,420, filed Aug. 11, 2014.
US Final Rejection, issued Nov. 17, 2014, from U.S. Appl. No. 14/227,272, filed Mar. 27, 2014.
US Final Rejection, issued Nov. 17, 2014, from U.S. Appl. No. 14/227,363, filed Mar. 27, 2014.
International Search Report, mailed Nov. 19, 2014, from PCT/US 14/50577 filed Aug. 11, 2014.
Stefan van der Burgh et al; "Complex coacervation core micelles as anti-fouling agents on silica and polystyrene surfaces"; Elsevier; Colloids and Surfaces A: Physiochem.Eng. Aspects 242 (2004); pp. 167-174; www.elsevier.com.
International Search Report of PCT Application No. PCT/US2011/29530, May 27, 2011 3 Pages.
International Search Report of PCT Application No. Pot/US2011/29 t59, Jun. 3, 2011, 4 Pages.
ACI (www.cleaninginstitute.org/clean_living/laundering-problems.aspx, retrieved Nov. 19, 2015, published online Feb. 1, 2001).
US Non-final Rejection, issued on Nov. 30, 2015, from U.S. Appl. No. 13/772,733, filed Feb. 21, 2013.
US Non-final Rejection, issued on Dec. 15, 2015, from U.S. Appl. No. 13/772,674, filed Feb. 21, 2013.
US Final Rejection, issued Jan. 29, 2015, from U.S. Appl. No. 13/772,674, filed Feb. 21, 2013.

\* cited by examiner

AQUEOUS COMPOSITIONS COMPRISING ASSOCIATIVE POLYELECTROLYTE COMPLEXES (PEC)

This application is a continuation-in-part of co-pending U.S. patent application entitled "Polyelectrolyte Complexes" and having Ser. No. 12/749,288, which was filed on Mar. 29, 2010.

BACKGROUND OF THE INVENTION

1. Field of the Invention

The present invention relates to aqueous compositions of associative polyelectrolyte complexes (PECs) which can clean a surface and/or provide surface protection to treated articles including reduced soiling tendency, reduced cleaning effort and improved soil repellency, as well as providing bacteriostatic properties to treated surfaces that thereby gain resistance to water, environmental exposure and microbial challenge.

2. Description of the Prior Art

Consumers are dissatisfied with their ability to prevent water and soils, such as water spots, soap scum, toothpaste, scale, greasy soils, brake dust, grime, rust, and toilet ring, from soiling and building up on household surfaces and other exposed materials. It would be desirable to have treatment means that would easily modify or enhance the surface protective properties of a wide variety of materials to retain and/or maintain their "like new" appearance and/or clean state and/or disinfected state for longer periods of time, particularly when exposed to water, soil and microbial challenge. It would further be desirable to have a treatment means compatible with cleaning aids, so that cleaning and treatment of soiled surfaces could be done either in conjunction or simultaneously with the treatment means providing enhanced protection including extended antimicrobial activity.

Consumers also desire cleaners and treatments that are convenient to use or that reduce cleaning effort (less surface scrubbing or buffing) during the initial cleaning or treatment, and which provide the benefit of reduced effort or increased speed of subsequent cleaning or treatment. Products used by professionals, such as janitorial services or automobile detailers, that provide reduced cleaning or treatment times are likewise of considerable value in reducing labor costs.

However, many commercial disinfectants employing the use of typical quaternary ammonium biocides deposited on surfaces to reduce microbial loads tend to leave the treated surfaces that are sticky to the touch and which attract dust and detritus leading to unsightly surfaces requiring frequent cleaning and reapplication to remain effective. There is a need for treatment compositions that provide stable, but thin and invisible layers or particles on treated surfaces with enhanced surface protective properties, such as reduced adhesion of soil, biological and environmental contaminants, or the ability to kill germs that are deposited onto the surfaces in a variety of ways, including airborne contaminants, food preparation, direct epidermal contact with humans or animals, and exposure to bodily fluids. There is a need for compositions that can also be employed to simultaneously clean and treat the surfaces so that separate cleaning and treatment steps are not required.

It is therefore an object of the present invention to provide compositions containing associative polyelectrolyte complexes capable of treating the surfaces of articles that overcome the disadvantages and shortcomings associated with prior art compositions. It is a further object of the present invention to provide compositions and means for the deposition of associative polyelectrolyte complexes (PECs) which can form densely packed uniform nanometer scale structures on treated surfaces when applied in the form of an aqueous treatment composition.

It is another object of the present invention to provide aqueous treatment compositions of associative polyelectrolyte complexes combined with additional cleaning adjuncts and/or biocides useful to effect the treatment of articles to provide treated surfaces having surface protection benefits such as reduced soiling tendency, reduced cleaning effort and improved soil repellency, as well as to provide bacteriostatic properties to treated surfaces that have good resistance to water and environmental exposure.

SUMMARY OF THE INVENTION

In accordance with the above objects and those that will be mentioned and will become apparent below, one aspect of the present invention is a treatment composition comprising: (i) at least one associative polyelectrolyte complex formed by combining a water soluble cationic first polyelectrolyte; and a water soluble second polyelectrolyte bearing groups of opposite charge to said first polyelectrolyte; wherein R, the molar ratio of charged groups present on said first polyelectrolyte to oppositely charged groups present on said second polyelectrolyte is between 0.10 to 20; (ii) at least one oxidant selected from the group consisting of: alkaline metal salts and/or alkaline earth metal salts of hypochlorous acid, hypochlorous acid, solubilized chlorine, any source of free chlorine, acidic sodium chlorite, active chlorine generating compound and any combinations or mixtures thereof; optionally, a buffering agent; optionally, a surfactant; and optionally, an antimicrobial agent.

In one embodiment of the invention, the composition may consist essentially of: (i) at least one associative polyelectrolyte complex formed by combining a water soluble cationic first polyelectrolyte; and a water soluble second polyelectrolyte bearing groups of opposite charge to said first polyelectrolyte; wherein R, the molar ratio of charged groups present on said first polyelectrolyte to oppositely charged groups present on said second polyelectrolyte is between 0.10 to 20; (ii) at least one oxidant selected from the group consisting of: alkaline metal salts and/or alkaline earth metal salts of hypochlorous acid, hypochlorous acid, solubilized chlorine, any source of free chlorine, acidic sodium chlorite, active chlorine generating compound and any combinations or mixtures thereof; optionally, a buffering agent; optionally, a surfactant; optionally, an antimicrobial agent; and optionally, an adjunct.

In another aspect of the invention, is a treatment composition and a method of forming a treated article, involving the steps of (a) applying a treatment composition to at least one surface of an article comprising a suitable substrate material; (b) allowing said treatment composition to deposit at least one layer comprising a plurality of associative polyelectrolyte complexes on said surface; and (c) removing said treatment composition from said surface by means selected from allowing the surface to drain, allowing the surface to dry, wiping the surface with a wiping implement, rinsing the surface with water, and combinations thereof; wherein said treatment composition comprises: (i) an aqueous composition comprising at least one associative polyelectrolyte complex formed by combining a water soluble cationic first polyelectrolyte; and a water soluble second polyelectrolyte bearing groups of opposite charge to said first polyelectrolyte; wherein R, the molar ratio of charged groups present on said first polyelectrolyte to oppositely charged groups present on said second polyelectrolyte is between 0.10 to 20; wherein said treatment composition further comprises: (ii) optionally, a buffering agent; (iii) optionally, a surfactant; (iv) optionally, a biocidal agent; and (v) optionally, an oxidant.

In another aspect of the present invention is a method of forming at least one associative polyelectrolyte complex by means of a mixing step that is accomplished without high shear mixing, including, but not limited to means of low energy mixing selected from liquid-to-liquid addition, stirring, static mixing, paddle mixing, low-shear mixing, and combinations thereof, wherein said low energy mixing is accomplished at temperatures between 10 to 45° C. In yet another aspect of the present invention, the method of forming at least one associative polyelectrolyte complex is done at a concentration of less than or equal to about 100 millimolar with respect to the total concentration of charged associating groups present on the polyelectrolytes making up a plurality of associative polyelectrolyte complexes.

In a further aspect of the present invention is a method of forming a plurality of associative polyelectrolyte complexes having an average aggregate size in solution of less than about 500 nanometers, or alternatively having an average $R_G$ and average $R_H$ value in solution of between about 20 nanometers to about 300 nanometers.

In one aspect of the present invention is a method of adding a surfactant to a treatment composition after formation of at leas t one associative polyelectrolyte complex in the treatment composition; wherein the surfactant is selected from the group consisting of water soluble and/or water dispersible anionic, cationic, zwitterionic, nonionic or amphoteric surfactants. In another aspect of the present invention is a method of adding either a biocide or an oxidant, or a combination thereof, to a treatment composition containing at least one associative polyelectrolyte complex to provide a treatment composition capable of deodorizing, sanitizing and/or disinfecting the surface of an article treated with said treatment composition containing the biocide or the oxidant; and optionally a method whereby the surface of the article is provided with an extended biocidal or oxidizing effect for a prolonged time after said treatment to provide at least one of a deodorizing, sanitizing and/or disinfecting benefit when exposed to a further source of microbial contaminants.

In a further aspect of the present invention, the method of forming a treated article involves a second treatment step comprising the step of applying to the surface of said article a disinfecting composition comprising a biocidal agent and optionally a cleaning adjunct; wherein a preformed layer of a plurality of associative polyelectrolyte complexes on said surface of said treated article thereby incorporates a sufficient amount of the biocidal agent present in the disinfecting composition so as to provide an effective amount of the biocidal agent on the surface during the second treatment step.

In another aspect of the present invention is a treatment composition and method of forming a treated article, wherein the surface of the treated article bears a plurality of associative polyelectrolyte complexes in the form of a layer which is non-permanent, invisible to the unaided human eye, capable of sequestering moisture from the atmosphere, and which is less than about 500 nanometers in thickness.

In yet another aspect of the present invention, the associative polyelectrolyte complexes are made by combining a cationic first polyelectrolyte and an oppositely charged second polyelectrolyte that are not selected from the group consisting of synthetic block copolymer, polymer fluorosurfactant derived from polymerization of a fluorinated oxetane, cross-linked polyacrylic acid, anionic complexing agent with a bulky molecule having an anionic group, silicone polymer, anionic latex, polyacrylate with an average molecular weight below about 10,000 Daltons, anionic polysaccharide containing glucoronic acid, N-acylchitosan with an C1-12 alkyl group, and a combination of chitosan and copolymers of acrylate and styrene monomers, and/or styrene derivatives, and/or combinations thereof.

In an aspect of the present invention, the first polyelectrolyte and the second polyelectrolyte are polymers that are completely soluble in water at a level of at least 10 g in 100 ml of water at a temperature of 25° C. In one aspect of the present invention, the associative polyelectrolyte complexes are formed using a first and a second polyelectrolyte that are selected from the group consisting of natural and/or naturally-derived polymers.

In a further aspect of the present invention, an aqueous treatment composition for treating the surface of an article is provided in which the treatment composition comprises (i) an aqueous composition comprising at least one associative polyelectrolyte complex formed by combining a water soluble cationic first polyelectrolyte; and a water soluble second polyelectrolyte bearing groups of opposite charge to said first polyelectrolyte; wherein the one polyelectrolyte present in molar excess is added in the form of a first aqueous solution during a mixing step to a second aqueous solution comprising the oppositely charged polyelectrolyte present in molar deficiency; wherein R, the molar ratio of charged groups present on said first polyelectrolyte to oppositely charged groups present on said second polyelectrolyte is between 0.10 to 10; wherein the treatment composition further comprises: (ii) a buffering agent; (iii) a surfactant; (iv) optionally, a biocidal agent; and (v) optionally, an oxidant; wherein said cationic first polyelectrolyte and said second polyelectrolyte are not synthetic block copolymers; and wherein said mixing step is accomplished without high shear mixing.

Further features and advantages of the present invention will become apparent to those of ordinary skill in the art in view of the detailed description of preferred embodiments below, when considered together with the attached claims.

DETAILED DESCRIPTION OF THE INVENTION

Before describing the present invention in detail, it is to be understood that this invention is not limited to particularly exemplified systems or process parameters that may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

In the instant application, effective amounts are generally those amounts listed as the ranges or levels of ingredients in the descriptions; which follow hereto. Unless otherwise stated, amounts listed in percentage ("%'s") are in weight percent (wt %), as based on 100% active of that particular component or ingredient present in the indicated formulation or composition.

As used herein, the term "polymer" and "polyelectrolyte" generally includes, but is not limited to, homopolymers, copolymers, such as for example, graft, random and alternating copolymers, terpolymers, etc. and blends and modifications thereof. Furthermore, unless otherwise specifically limited, the term "polymer" and "polyelectrolyte" shall include all possible geometrical configurations of the molecule. These configurations include, but are not limited to isotactic, syndiotactic and random symmetries. In general, the term "polyelectrolyte", as used herein, means and is meant to mean a polymer having at least one permanent charge, of either an anionic or cationic nature, when dissolved in an aqueous solution. As used herein, the term "polyelectrolyte" also means and is meant to mean a polymer capable of forming a charge, of either an anionic or cationic nature, when dissolved in an aqueous solution whose pH has been adjusted by some means including the addition of an acid, a base or suitable buffering agent, so as to form a net anionic or cationic charge on the polymer in water.

Molecular weights are generally expressed in terms of the number of moles per gram of the compound (MW) and in the case of polymers and polyelectrolytes are generally expressed in terms of an average molecular weight with respect to the plurality of individual polymers present within a polymer solution expressed as Daltons (Da).

The term "water soluble" as used herein, means and is meant to mean and include materials, particularly the polyelectrolytes of the present invention, which are sufficiently soluble or dispersible in water to create an optically clear, non-separating and non-precipitating aqueous solution when present in water at a level of at least about 10 g in 100 ml of water at room temperature (25° C.), alternatively, at least about 20 g in 100 ml of water, or yet alternatively at least about 25 g in 100 ml of water at room temperature.

The term "comprising", which is synonymous with "including," "containing," or "characterized by," is inclusive or open-ended and does not exclude additional, unrecited elements or method steps. See MPEP 2111.03. See, e.g., *Mars Inc.* v. *H.J. Heinz Co.*, 377 F.3d 1369, 1376, 71 USPQ2d 1837, 1843 (Fed. Cir. 2004) ("like the term 'comprising,' the terms 'containing' and 'mixture' are open-ended."). *Invitrogen Corp.* v. *Biocrest Mfg., L.P.*, 327 F.3d 1364, 1368, 66 USPQ2d 1631, 1634 (Fed. Cir. 2003) ("The transition 'comprising' in a method claim indicates that the claim is open-ended and allows for additional steps."); *Genentech, Inc.* v. *Chiron. Corp.*, 112 F.3d 495, 501, 42 USPQ2d 1608, 1613 (Fed. Cir. 1997) See MPEP 2111.03. ("Comprising" is a term of art used in claim language which means that the named elements are essential, but other elements may be, added and still form a construct within the scope of the claim.); *Moleculon Research Corp.* v. *CBS, Inc.*, 793 F.2d 1261, 229 USPQ 805 (Fed. Cir. 1986); *In re Baxter*, 656 F.2d 679, 686, 210 USPQ 795, 803 (CCPA 1981); *Ex parte Davis*, 80 USPQ 448, 450 (Bd. App. 1948). See MPEP 2111.03.

The term "consisting essentially of" as used herein, limits the scope of a claim to the specified materials or steps "and those that do not materially affect the basic and novel characteristic(s)" of the claimed invention. *In re Herz*; 537 F.2d 549, 551-52, 190 USPQ 461, 463 (CCPA 1976) (emphasis in original). See MPEP 2111.03.

The term "consisting of" as used herein, excludes any element, step, or ingredient not specified in the claim. In re Gray 53 F.2d 520, 11 USPQ 255 (CCPA 1931); Ex Parte Davis, 80 USPQ 448, 450 (Bd. App. 1948). See MPEP 2111.03.

ASSOCIATIVE POLYELECTROLYTE COMPLEXES

Figure 1:
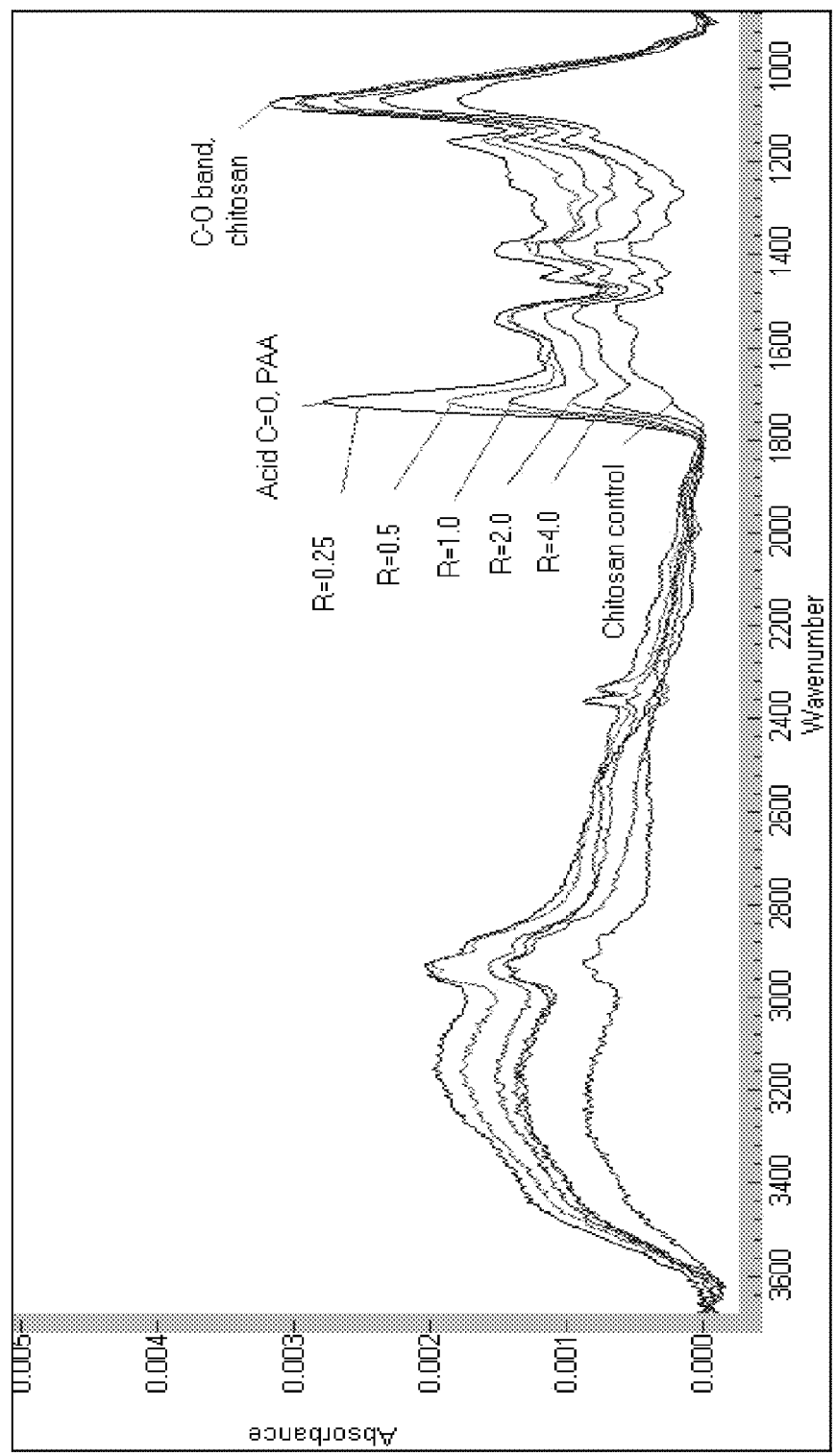
FIG. 1 illustrates some examples of FT-IR spectra of adsorbed layers of the associative polyelectrolyte complexes (PECs) formed, on a Ge (germanium) surface exposed 5 minute to an associative PECs formulations of 1.3 mM total poly(acrylic acid) (PAA) and chitosan and 0.7 wt % citric acid followed by 50 water rinses and dry nitrogen purge. R value indicated of separate treatment systems. Acid carbonyl band labeled as "Acid C=O, PAA" and C—O stretching band labeled as "C—O band, chitosan".
Figure 2:
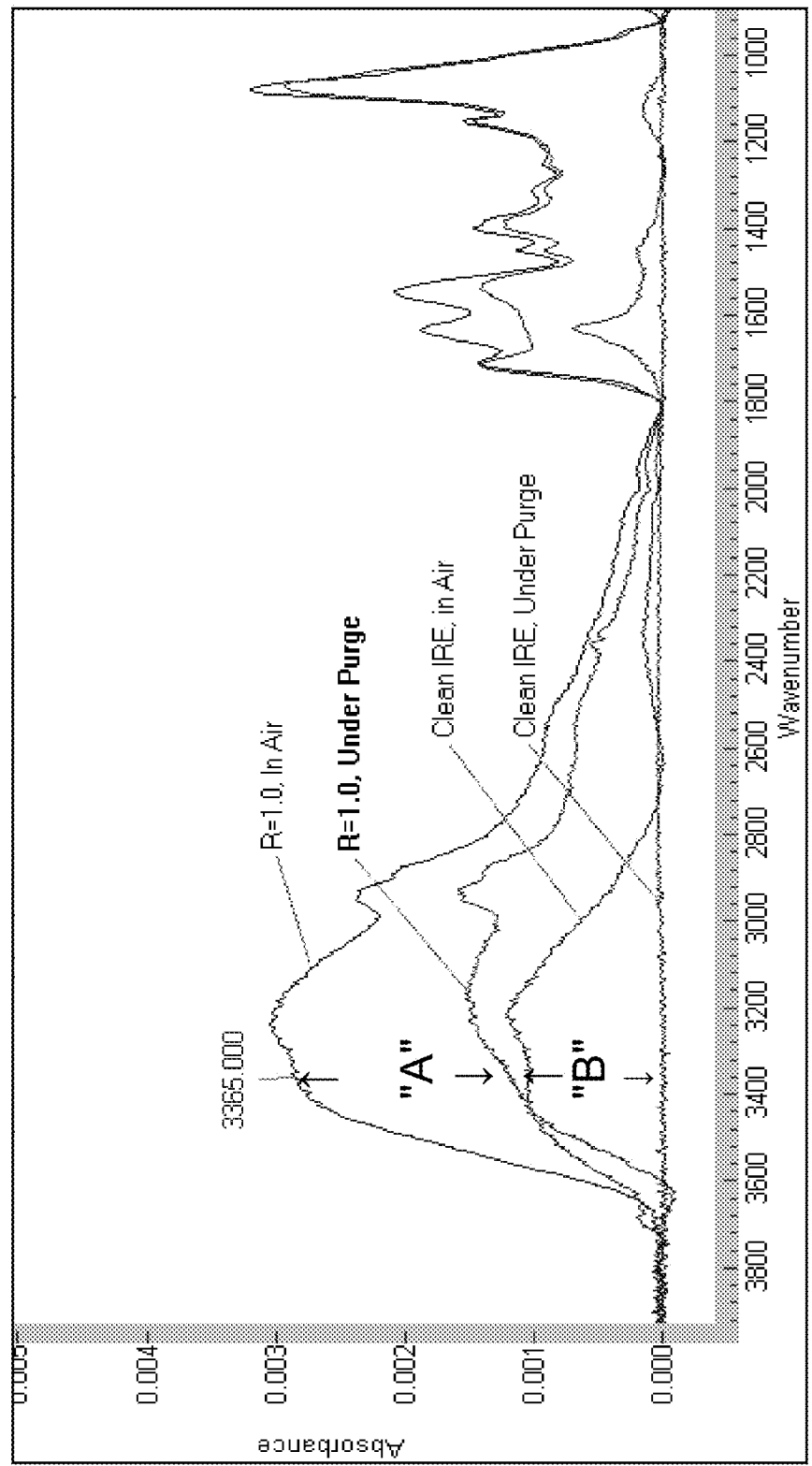
FIG. 2 shows the spectra of the clean IRE surface under the dry nitrogen purge and in air. H—O—H stretching band of liquid water is 3600 and 3000 wavenumber ($cm^{-1}$). Also shown is a spectrum of a associative PEC layer, labeled "R=1.0, Under Purge", obtained under dry nitrogen purge on the same Ge surface after exposing the IRE to a Chitosan/PAA PEC solution with R=1.0, followed by 50 rinses. Also shown is the spectrum of the same associative PEC layer in air, immediately after removal of the dry nitrogen purge, labeled "R=1.0, In Air".

The associative polyelectrolyte complexes (PECs) of the present invention have been found to exhibit surprisingly rapid adsorption onto a wide variety of surfaces, even in the presence of other surface-active agents commonly employed in cleaning and treatment formulations, to yield thin, invisible layers on the treated surfaces. The adsorption of the associative PECs proceeds, even in the presence of other surface-active agents.

The associative PECs of the present invention comprise at least two different water-soluble polyelectrolytes, each of which bears electrostatically charged groups, or groups capable of developing a charge (capable of ionization), in which the overall net charges on the two polymers are opposite or are capable of becoming opposite through manipulation of the pH of the aqueous phase.

The associative PECs of the present invention are assembled in such a way that they have an average aggregate size in solution of less than about 500 nm, preferably less than 400 nm, more preferably less than 300 nm, even more preferably less than 200 nm, and most preferably less than about 100 nm in diameter. The particle size and molecular weights of the associative PECs can be measured via static light scattering (SLS), as described herein. In the initial absence of any charged surfactants and/or surface active adjuncts, it has, been discovered that stable associative PECs may be produced by the blending of aqueous stock solutions of the oppositely charged polymers such that the total polymer concentration in the mixture is less than 100 mM, preferably less than 75 mM, more preferably less than 50 mM, and most preferably less than 10 mM, and further providing that a specific mixing order as described herein below is followed in the preparation of the associative PECs.

The blending of the two polymer stock solutions comprising a first polyelectrolyte (Polymer A) and a second polyelectrolyte (Polymer B) bearing oppositely charged groups with respect to the overall charge of Polymer A, can be accomplished by first diluting a stock solution of Polymer A in the aqueous medium in a tank, and then adding, with simple low-shear agitation appropriate for the tank size, a stock solution of Polymer B until the total polymer concentration reaches the desired final concentration. It is preferred to add the stock solution of the polyelectrolyte which will be in molar excess to an appropriately diluted stock solution of the oppositely charged polyelectrolyte which will be in molar deficiency in the final solution.

The blending or mixing step may readily be accomplished by means of low energy mixing selected from liquid-to-liquid addition, stirring, static mixing, paddle mixing, low shear mixing, and combinations thereof. Further, the blending or mixing step does not require the use of high temperatures to improve the solubility of the polyelectrolytes and can readily be accomplished at most ambient temperatures or with moderate heating, such as for example between temperatures of 10 to 45° C., or alternatively between temperatures of 10 to 35° C., or between 15 to 35° C. or between 15 to 25° C., or between 20 to 30° C.

Surprisingly, since macroscopic solids and gels do not form under these conditions, high shear or high energy mixing is not required to form the associative PECs, even for compositions in which there are equal numbers of oppositely charged groups introduced into the aqueous solution, i.e., even for compositions reaching values of R, as defined below, equal to 1.0.

A convenient way to express the composition of the associative PECs is to calculate the ratio of the moles or number of cationic charges to corresponding moles or number of anionic charges present in the solution, based on the relative amounts of the polymers added to the bulk solution. Herein below, the parameter "R" is used to denote the molar ratio of cationic (or potentially cationic) groups to that of anionic (or potentially anionic) groups of the two respective polyelectrolytes comprising the associative PECs of the present invention, where accordingly:

$$R=Q^+/Q^-$$

where $Q^+$ is the number or moles of cationic charges, $Q^-$ is the number or moles of anionic charges; wherein $$Q^+ = (C_{cationic})^*(F_{cationic})^*(Q_{cationic})/(M_{cationic})$$

where $C_{cationic}$ is the concentration of cationic polymer in wt %, $F_{cationic}$ is the weight fraction cationic monomer in total cationic polymer weight, thus being between 0 and 1, $Q_{cationic}$ is the number of charges per cationic monomer unit, $M_{cationic}$ is the molecular weight of the monomer unit in polymerized form; and correspondingly:

$$Q^- = (C_{anionic})^*(F_{anionic})^*(Q_{anionic})/(M_{anionic})$$

where $C_{anionic}$ is the concentration of anionic polymer in wt %, $F_{anionic}$ is the weight fraction anionic monomer in total anionic polymer weight, thus being between 0 and 1, $Q_{anionic}$ is the number of charges per anionic monomer unit, and $M_{anionic}$ is the molecular weight of the monomer unit in polymerized form.

Polyelectrolytes Suitable for Associative PECs Formulations
Natural Cationic Polymers Any natural cationic polymer may be employed. Chitosan is a preferred natural polymer, but also acceptable in addition to the natural polysaccharide obtained by deacetylation of chitin (from marine source) or by direct isolation from fungi, are those synthetically produced β-1,4-poly-D-glucosamines and derivatives thereof that are isomers or structurally similar to natural chitosan. The chitosan polymers of the invention can have substantially protonated glucosamine monomeric units, improving polymer water solubility, for example, N-hydroxybutyl chitosans described in U.S. Pat. No. 4,931,271 to Lang et al. and chitosan pyrithione derivatives described in U.S. Pat. No. 4,957,908 to Nelson. Additional polysaccharides suitable for use in the composition according to the invention include, but are not limited to, cationic guar, hydroxypropyl guar and starch bearing cationic charges added by chemical quaternization (for example, but not limited to, alkoxylation with a quaternary epoxide).

When present the natural cationic polymer level in the compositions of the present invention is typically from about 0.001 wt % to about 5.0 wt %, or from about 0.01 wt % to about 2.5 wt %, or from about 0.01 wt % to about 1.0 wt %, or from about 0.1 wt % to about 0.50 wt %.

Synthetic Cationic Polymers

Suitable cationic polymers include homopolymers or copolymers of monomers having a permanent cationic charge or monomers capable of forming a cationic charge in solution upon protonation. Examples of permanently cationic monomers include, but are not limited to, diallyl dimethyl ammonium salts (such as the chloride salt, referred to herein as DADMAC) quaternary ammonium salts of substituted acrylamide, methacrylamide, acrylate and methacrylate, such as trimethylammoniumethyl methacrylate, trimethylammoniumpropyl methacrylamide, trimethylammoniumethyl methacrylate, trimethylammoniumpropyl acrylamide, 2-vinyl N-alkyl quaternary pyridinium, 4-vinyl N-alkyl quaternary pyridinium, 4-vinylbenzyltrialkylammonium, 2-vinyl piperidinium, 4-vinyl piperidinium, 3-alkyl 1-vinyl imidazolium, and the ionene class of internal cationic monomers as described by D. R. Berger in *Cationic Surfactants, Organic Chemistry*, edited by J. M. Richmond, Marcel Dekker, New York, 1990, ISBN 0-8247-8381-6, which is incorporated herein by reference The counterion of the cationic co-monomer can be selected from, for example, chloride, bromide, iodide, hydroxide, phosphate, sulfate, hydrosulfate, ethyl sulfate, methyl sulfate, formate, and acetate.

Examples of monomers that are cationic on protonation include, but are not limited to, acrylamide, N,N-dimethylacrylamide, N,N di-isopropylacryalmide, N-vinylimidazole, N-vinylpyrrolidone, vinyl pyridine N-oxide, ethyleneimine, dimethylaminohydroxypropyl diethylenetriamine, dimethylaminoethyl methacrylate, dimethylaminopropyl methacrylamide, dimethylaminoethyl acrylate, dimethylaminopropyl acrylamide, 2-vinyl pyridine, 4-vinyl pyridine, 2-vinyl piperidine, 4-vinylpiperidine, vinyl amine, diallylamine, methyldiallylamine, vinyl oxazolidone; vinyl methyoxazolidone, and vinyl caprolactam.

Monomers that are cationic on protonation typically contain a positive charge over a portion of the pH range of 2-11. Such suitable monomers are also presented in *Water-Soluble Synthetic Polymers: Properties and Behavior*, Volume II, by P. Molyneux, CRC Press, Boca Raton, 1983, ISBN 0-8493-6136. Additional monomers can be found in the *Interna-* tional *Cosmetic Ingredient Dictionary*, 5th Edition, edited by J. A. Wenninger and G. N. McEwen, The Cosmetic, Toiletry, and Fragrance Association, Washington D.C., 1993, ISBN 1-882621-06-9. A third source of such monomers can be found in *Encyclopedia of Polymers and Thickeners for Cosmetics*, by R. Y. Lochhead and W. R. Fron, Cosmetics & Toiletries, vol. 108, May 1993, pp 95-135. All three references are hereby incorporated herein in their entirety.

Cationic polymers may also include other monomers, for example monomers having an uncharged hydrophilic or hydrophobic group. Suitable copolymers contain acrylamide, methacrylamide and substituted acrylamides and methacrylamides, acrylic and methacrylic acid and esters thereof. Suitable synthetic methods for these copolymers are described, for example, in Kirk-Othmer, *Encyclopedia of Chemical Technology*, Volume I, Fourth Ed., John Wiley & Sons.

The cationic polymer level in the compositions of the present invention is typically from about 0.001 wt % to about 5.0 wt %, or from about 0.01 wt % to about 2.5 wt %, or from about 0.01 wt % to about 1.0 wt %, or from about 0.1 wt % to about 0.50 wt %.

Anionic Polymers

Suitable anionic polymers include, but are not limited to, polycarboxylate polymers and copolymers of acrylic acid and maleic anhydride, or alkali metal salts thereof, such as the sodium and potassium salts. Suitable are copolymers of acrylic acid or methacrylic acid with vinyl ethers, such as, for example, vinyl methyl ether, vinyl esters, ethylene, propylene and styrene. Also suitable are polymers containing monomers capable of taking on an anionic charge in aqueous solutions when dissolved in water that has been adjusted to an appropriate pH using an acid, a base a buffer or combination thereof. Examples include, but are not limited to, acrylic acid, maleic acid, methacrylic acid, ethacrylic acid, dimethylacrylic acid, maleic anhydride, succinic anhydride, vinylsulfonate, cyanoacrylic acid, methylenemalonic acid, vinylacetic acid, allylacetic acid, ethylidineacetic acid, propylidineacetic acid, crotonic acid, fumaric acid, itaconic acid, sorbic acid, angelic acid, cinnamic acid, styrylacrylic acid, citraconic acid, glutaconic acid, aconitic acid, phenylacrylic acid, acryloxypropionic acid, citraconic acid, vinylbenzoic acid, N-vinylsuccinamidic acid, mesaconic acid, methacroylalanine, acryloylhydroxyglycine, sulfoethyl methacrylate, sulfopropyl acrylate, and sulfoethyl acrylate. Suitable acid monomers also include styrenesulfonic acid, acrylamide methyl propane sulfonic acid, 2-methacryloyloxy-methane-1-sulfonic acid, 3-methacryloyloxy-propane-1-sulfonic acid, 3-(vinyloxy)-propane-1-sulfonic acid, ethylenesulfonic acid, vinyl sulfuric acid, 4-vinylphenyl sulfuric acid, ethylene phosphonic acid and vinyl phosphoric acid. Examples of commercially available products are Sokalan CP5® and PA30® from BASF, Alcosperse 175® or 177® from Alco and LMW 45N® and SPO2N® from Norsohaas. Also suitable are natural anionic polymers, including but not limited to saccharinic gums such as alginates, xanthates, pectins, carrageenans, guar, carboxymethyl cellulose, and scleroglucans.

The anionic polymer level in the compositions of the present invention is typically from about 0.001 wt % to about 5.0 wt %, or from about 0.01 wt % to about 2.5 wt %, or from about 0.01 wt % to about 1.0 wt %, or from about 0.1 wt % to about 0.50 wt %.

Buffer/Electrolyte

Buffers, buffering agents and pH adjusting agents, when used, include, but are not limited to, organic acids, mineral acids, alkali metal and alkaline earth salts of silicate, metasilicate, polysilicate, borate, carbonate, carbamate, phosphate, polyphosphate, pyrophosphates, triphosphates, tetraphosphates, ammonia, hydroxide, monoethanolamine, monopropanolamine, diethanolamine, dipropanolamine, triethanolamine, and 2-amino-2methylpropanol. In one embodiment, preferred buffering agents for compositions of this invention include but are not limited to; dicarboxylic acids, such as, succinic acid and glutaric acid. Some suitable nitrogen-containing buffering agents are amino acids such as lysine or lower alcohol amines like mono-, di-, and triethanolamine. Other nitrogen-containing buffering agents are Tri(hydroxymethyl) amino methane (HOCH2)3CNH3 (TRIS), 2-amino-2-ethyl-1,3-propanediol, 2-amino-2-methyl-propanol, 2-amino-2-methyl-1,3-propanol, disodium glutamate, N-methyl diethanolamide, 2-dimethylamino-2-methylpropanol (DMAMP), 1,3-bis (methylamine)-cyclohexane, 1,3-diamino-propanol N,N'-tetra-methyl-1,3-diamino-2-propanol, N,N-bis(2-hydroxyethyl)glycine (bicine) and N-tris(hydroxymethyl) methyl glycine (tricine). Other suitable buffers include ammonium carbamate, citric acid, and acetic acid. Mixtures of any of the above are also acceptable. Useful inorganic buffers/alkalinity sources include ammonia, the alkali metal carbonates and alkali metal phosphates, e.g., sodium carbonate, sodium polyphosphate. For additional buffers see McCutcheon's Emulsifiers and Detergents, North American Edition, 1997, McCutcheon Division, MC Publishing Company Kirk and WO 95/07971 both of which are incorporated herein by reference.

In one embodiment of the invention, when hypochlorous acid is used, an acid may be beneficial to stabilize the pH and maintain the desired ratio of hypochlorous acid to hypochlorite anion. In some cases, the acid may be added to a solution containing hypochlorite anion to convert this anion to hypochlorous acid. An acid may also be used to control the formation of chlorine dioxide from a chlorite salt. Acid may also be used with peroxygen compounds to control stability or reactivity. They may also be added for cleaning and removal of soils such as hard water deposits and rust. Exemplary acids include, but are not limited to inorganic acids such as hydrochloric acid or sulfuric acid; and organic acids such as sulfonic acid, polysulfonic acid, monocarboxylic acid, dicarboxylic acid, polycarboxylic acid, acid sulfate, acid phosphate, phosphonic acid, aminocarboxylic acid and mixtures thereof. Specific examples of acids, include but are not limited to, acetic acid, succinic acid, glutaric acid, adipic acid, polyacrylic acid, sodium bisulfate, 3-pyridine sulfonic acid, dodecyl benzene sulfonic acid, polyacrylic acid, and mixtures thereof. Sodium, potassium and any other salt of any of these acids or mixtures thereof may also be included to achieve the desired pH and create a buffer system that resists changes in pH.

Buffers and electrolytes "screen" the interactions between the polymers of the associative PECS of the present invention, and thus may be used to modify phase behavior, such as preparing formulations "close" to a coacervate phase boundary, which is useful because the complexes become sufficiently large (up to about 500 nm diameter) or high enough in total molecular weight to exhibit enhanced adsorption onto surfaces. Any suitable electrolyte salt known in the art may be used to control ionic strength and/or pH of the final formulations. When used herein the buffer or electrolyte salt is preferably present at a concentration of from about 0.001 wt % to about 5 wt %, more preferably 0.05 wt % to about 1 wt %, even more preferably from about 0.05 wt % to about 0.5 wt %, and most preferably 0.1 wt % to about 0.5 wt %.

Antimicrobial Agents

The compositions of the present invention can also, optionally, contain antimicrobial agents or biocidal agents. Such antimicrobial agents can include, but are not limited to, alcohols, chlorinated hydrocarbons, organometallics, halogen-releasing compounds, metallic salts, pine oil, organic sulfur compounds, iodine compounds, silver nitrate, quaternary ammonium compounds (quats), chlorhexidine salts, and/or phenolics. Antimicrobial agents suitable for use in the compositions of the present invention are described in U.S. Pat. Nos. 5,686,089; 5,681,802, 5,607,980, 4,714,563; 4,163,800; 3,835,057; and 3,152,181, all of which are herein incorporated by reference in their entirety. Also useful as antimicrobial agents are the so-called "natural" antibacterial actives, referred to as natural essential oils. These actives derive their names from their natural occurrence in plants. Suitable antimicrobial agents include alkyl alpha-hydroxyacids, aralkyl and aryl alpha-hydroxyacids, polyhydroxy alpha-hydroxyacids, polycarboxylic alpha-hydroxyacids, alpha-hydroxyacid related compounds, alpha-ketoacids and related compounds, and other related compounds including their lactone forms. Preferred antimicrobial agents include, but are not limited to, alcohols, chlorinated hydrocarbons, organometallics, halogen-releasing compounds, metallic salts, pine oil, organic sulfur compounds, iodine, compounds, antimicrobial metal cations and/or antimicrobial metal cation-releasing compounds, chitosan, quaternary alkyl ammonium biocides, phenolics, germicidal oxidants, germicidal essential oils, germicidal botanical extracts, alpha-hydroxycarboxylic acids, and combinations thereof. When incorporated herein the antimicrobial agent is preferably present at a concentration of from about 0.001 wt % to about 5 wt %, more preferably 0.05 wt % to about 1 wt %, even more preferably from about 0.05 wt % to about 0.5 wt %, and most preferably 0.1 wt % to about 0.5 wt %.

Surfactants

The compositions of the present invention may contain surfactants selected from nonionic, anionic, cationic, ampholytic, amphoteric and zwitterionic surfactants and mixtures thereof. A typical listing of anionic, ampholytic, and zwitterionic classes, and species of these surfactants, is given in U.S. Pat. No. 3,929,678 to Laughlin and Heuring. A list of suitable cationic surfactants is given in U.S. Pat. No. 4,259,217 to Murphy, which is hereby incorporated by reference. The surfactants may be present at a level of from about 0% to 90%, or from about 0.001% to 50%, or from about 0.01% to 25% by weight. Alternatively, surfactants may be present at a level of from about 0.1 to 10% by weight, or from about 0.1 to 5% by weight, or from about 0.1 to 1% by weight.

Solvent

Water may be used as a solvent alone, or a combination with any suitable organic solvents may be present in the compositions of the present invention include, but are not limited to, $C_{1-6}$ alkanols, $C_{1-6}$ diols, $C_{1-10}$ alkyl ethers of alkylene glycols, $C_{3-24}$ alkylene glycol ethers, polyalkylene glycols, short chain carboxylic acids, short chain esters, isoparafinic hydrocarbons, mineral spirits, alkylaromatics, terpenes, terpene derivatives, terpenoids, terpenoid derivatives, formaldehyde, and pyrrolidones. Alkanols include, but are not limited to, methanol, ethanol, n-propanol, isopropanol, butanol, pentanol, and hexanol, and isomers thereof. In one embodiment of the invention, water comprises at least 80% of the composition by weight, or at least 90% of the composition by weight or at least 95% of the composition by weight. In another embodiment of the invention, the organic solvents can be present at a level of from 0.001% to 10%, or from 0.01% to 10%, or from 0.1% to 5% by weight, or from 1% to 2.5% by weight.

Oxidants

The compositions of the present invention can also, optionally, contain oxidants and/or bleaching agents. Preferred oxidants include, but are not limited to, hydrogen peroxide, alkaline metal salts and/or alkaline earth metal salts of hypochlorous acid, hypochlorous acid, solubilized chlorine, any source of free chlorine, solubilized chlorine dioxide, acidic sodium chlorite, active chlorine generating compounds, active oxygen generating compounds, chlorine-dioxide generating compounds, solubilized ozone, sodium potassium peroxysulfate, sodium perborate, and combinations thereof. The oxidant can be present at a level of from 0.001% to 10%, or from 0.01% to 10%, or from 0.1% to 5% by weight, or from 0.5% to 2.5% by weight.

Additional Ingredients

The compositions of the present invention may optionally contain one or more of the following adjuncts: stain and soil repellants, lubricants, odor control agents, perfumes, fragrances and fragrance release agents, and bleaching agents. Other adjuncts include, but are not limited to, acids, bases, dyes and/or colorants, solubilizing materials, stabilizers, thickeners, defoamers, hydrotropes, cloud point modifiers, preservatives, and other polymers.

Methods of Use

The compositions of the present invention may be used by distributing, e.g., by placing the aqueous solution into a dispensing means, preferably a spray dispenser and spraying an effective amount onto the desired surface or article. An effective amount as defined herein means an amount sufficient to modify the surface of the article to achieve the desired benefit, for example, but not limited to soil repellency, cleaning and/or disinfectancy. Distribution can be achieved by using a spray device, such as a trigger sprayer or aerosol, or by other means including, but not limited to a roller, a pad, a wipe or wiping implement, sponge, etc.

In another embodiment, a surface, an article or a device may be treated with the compositions of the present invention by immersing them or exposing the desired portion of the article or device to be treated to a bulk liquid solution containing the inventive associative PECs in the form of a treatment composition. Suitable immersion methods include baths, dipping tanks, wet padding and wet rolling application means common to the art. Such means are also suitable for forming premoistened wipes wherein a carrier substrate such as a woven material (cloth, towel, etc) or a non-woven material (paper towel, tissue, toilet tissue, bandage) is dipped or padded with the inventive associative PECs in the form of a treatment composition.

EXAMPLES

The associative PECs of the present invention are very effective for increasing the hydrophilic character of surfaces because the adsorbed layer formed from exposing surfaces to the associative PECs takes up water molecules from the ambient atmosphere. Confirmation of the uptake of water molecules by the adsorbed layers is possible through the use of FT-IR (Fourier Transform Infrared) spectroscopy.

The following examples are provided to illustrate embodiments of the present invention including compositions, methods of formulation compositions, methods of use and methods of treating surfaces with formulations containing the novel associative polyelectrolyte complexes (PECs) described and claimed herein.

Example 1

Small Scale Preparation of PAA and Chitosan Stock Solutions

A series of PAA/Chitosan PECs was prepared at several R values via gentle mixing using a magnetic stir bar for 1-2 minutes while stirring the solution, the minor polymeric component being placed in the vessel first as designated in the Table 1A with "1" followed by the major polymeric component added to the minor component solution designated with a "2" next to the weight used. The orders of addition change, of course, depending on the desired R value. The resulting associative PEC solutions were allowed to stir overnight and yielded clear solutions in all cases.

TABLE 1A

Compositions of Chitosan/PAA PECs

| Formulation # | R (a) | Stock A (mL) (b) | Stock B (mL) (c) | 20 wt % Citric Acid (mL) (d) | H$_2$O (mL) | Total concentration charged groups (mM) |
|---|---|---|---|---|---|---|
| SCPAA1 | 0.25 | 0.4515 (1) | 0.7615 (2) | 0.5524 | 16.7580 | 1.29 |
| SCPAA2 | 0.51 | 0.7505 (1) | 0.6319 (2) | 0.4972 | 16.4492 | 1.30 |
| SCPAA3 | 0.77 | 0.9731 (1) | 0.5419 (2) | 0.4370 | 16.5710 | 1.29 |
| SCPAA4 | 1.05 | 1.1382 (1) | 0.4661 (2) | 0.3967 | 16.5342 | 1.28 |
| SCPAA5 | 1.27 | 1.2580 (2) | 0.4238 (1) | 0.3728 | 16.4988 | 1.30 |
| SCPAA6 | 1.55 | 1.3408 (2) | 0.3714 (1) | 0.3502 | 16.4406 | 1.28 |
| SCPAA7 | 1.78 | 1.4312 (2) | 0.3446 (1) | 0.3316 | 16.4275 | 1.29 |
| SCPAA8 | 2.05 | 1.5124 (2) | 0.3164 (1) | 0.3207 | 16.3751 | 1.30 |
| SCPAA9 | 3.15 | 1.6960 (2) | 0.2306 (1) | 0.2641 | 16.3056 | 1.29 |
| SCPAA10 | 4.05 | 1.7941 (2) | 0.1896 (1) | 0.2463 | 16.2738 | 1.29 |

(a) R = [Cationic amine groups from chitosan]/[Anionic acid groups from PAA]
(b) 0.2 wt % Federal Laboratories chitosan
(c) Alcosperse 465 PAA providing 33.1 mM charged acrylate groups
(d) Providing total of 0.7 wt % citric acid at a pH of 2.2 in all final formulations.

Large Scale Preparation of Chitosan/PAA PECs

A series of PAA/Chitosan PECs was prepared at several R values in approximately 0.7 wt % citric acid at a pH of 2.2 and can be found below in Table 1B.

TABLE 1B

Compositions of Chitosan/PAA PECs

| Formulation # | R (3) | Aldrich Chitosan Stock A (mL) | Alcosperse 465 PAA Stock B (mL) | 10 wt % Citric Acid (mL) | H$_2$O (mL) | Total concentration charged groups (mM) |
|---|---|---|---|---|---|---|
| CPAA 1 | 0.25 | 8.2600 (1) | 9.4500 (2) | 19.8900 | 263.4200 | 1.30 |
| CPAA 2 | 0.50 | 13.8000 (1) | 7.91 (2) | 17.4400 | 261.8100 | 1.30 |
| CPAA 3 | 0.75 | 17.7100 (1) | 6.78 (2) | 15.7500 | 260.6800 | 1.30 |
| CPAA 4 | 1.00 | 20.6500 (1) | 5.95 (2) | 14.2300 | 260.0600 | 1.31 |
| CPAA 5 | 1.26 | 23.0000 (2) | 5.25 (1) | 13.3900 | 259.2200 | 1.30 |
| CPAA 6 | 1.49 | 24.6800 (2) | 4.74 (1) | 12.5300 | 258.8700 | 1.30 |
| CPAA 7 | 1.76 | 26.2000 (2) | 4.28 (1) | 11.8400 | 258.4800 | 1.30 |
| CPAA 8 | 2.01 | 27.5100 (2) | 3.93 (1) | 11.3400 | 258.0500 | 1.30 |
| CPAA 9 | 3.00 | 31.0300 (2) | 2.97 (1) | 9.7500 | 257.0800 | 1.30 |
| CPAA 10 | 4.04 | 32.9000 (2) | 2.34 (1) | 8.8200 | 256.6900 | 1.30 |

(1) Minor polymeric component
(2) Major polymeric component
(3) R = [Cationic Amine groups from chitosan]/[Anionic Acid groups from PAA]

FT-IR spectroscopy can be used to characterize extremely thin layers of materials on hard surfaces. It is known in the art that it is convenient to use an optical accessory based on the principle of attenuated total reflectance (ATR) in such FT-IR work. FT-IR spectroscopy is described in *Fourier Transform Infrared Spectrometry*, by P. R. Griffiths. ATR optical accessories are described in *Internal Reflection Spectroscopy*, by N. J. Harrick, Interscience Publishers, 1967, and *Internal Reflection Spectroscopy Review and Supplement*, by F. M. Mirabella Jr., N. J. Harrick, Editor, Harrick Scientific Corporation, 88 Broadway, Box 1288, Ossining, N.Y. 10562. The optical accessory used in the measurements described herein was a "Horizon", available from Harrick Scientific Corporation, equipped with an internal reflection element (IRE) constructed from Ge.

The hydrophilic modification of a surface by some of the associative PECS described in Tables 1A and 1B were investigated with FT-IR spectroscopy using a clean Ge IRE for which a background absorbance spectrum under dry nitrogen purge was first recorded, as well as a "blank" for the particular IRE in its clean state in contact with the ambient atmosphere with the current humidity. The intensity of the absorbance band at 3365 cm$^{-1}$, which is due to the H—O—H stretching band of liquid water in the spectrum recorded, is measured to find the relative amount of water on the IRE surface, recorded in Table 1C below as the "B" values. The magnitude of the bands in all of the FT-IR spectra in this specification are expressed in milli-Absorbance Units (mAU), which are linearly related to concentration at the IRE surface.

The uptake of water by the extremely thin adsorbed layers is very rapid, and can be readily observed by the changes in the FT-IR spectra obtained with and without the dry purge. The difference is directly proportional to the amount of water uptake achieved by the adsorbed layer and are presented in Table 1C below as the "A" values. Finally, the increase in the surface water contents due to the presence of the adsorbed associative PEC layer is shown below in Table as value "C", computed from "A"-"B".

TABLE 1C

Chitosan/PAA PECS

| Formulation # | R | Number of Rinses | "A" Modified surface Water Uptake (mAU) | "B" IRE Water Uptake (mAU) | "C" Water uptake in PEC layer (mAU) |
|---|---|---|---|---|---|
| CPAA-10 | 4.04 | 10 | 1.453 | 1.046 | 0.407 |
| CPAA-10 | 4.04 | 50 | 1.417 | 1.046 | 0.371 |
| CPAA-4 | 1.0 | 10 | 1.567 | 1.012 | 0.555 |
| CPAA-4 | 1.0 | 50 | 1.659 | 1.012 | 0.647 |
| CPAA-2 | 0.5 | 10 | 1.507 | 1.127 | 0.38 |
| CPAA-2 | 0.5 | 50 | 1.602 | 1.127 | 0.475 |
| CPAA-3 | 0.76 | 10 | 1.749 | 1.083 | 0.666 |
| CPAA-3 | 0.76 | 50 | 1.855 | 1.083 | 0.772 |
| CPAA-8 | 2.01 | 10 | 1.686 | 1.253 | 0.433 |
| CPAA-8 | 2.01 | 50 | 1.722 | 1.253 | 0.469 |
| CPAA-9 | 3.0 | 10 | 1.69 | 1.363 | 0.327 |
| CPAA-9 | 3.0 | 50 | 1.564 | 1.363 | 0.201 |
| CPAA-10 | 4.04 (1) | 10 | 1.997 | 1.574 | 0.423 |
| CPAA-10 | 4.04 (1) | 50 | 2.00 | 1.574 | 0.426 |
| CPAA-1 | 0.25 (1) | 10 | 2.104 | 1.421 | 0.683 |
| CPAA-1 | 0.25 (1) | 50 | 2.107 | 1.421 | 0.686 |
| CPAA-1 | 0.25 (1) | 100 | 1.893 | 1.421 | 0.472 |

(1) Sample measurements obtained after 30 minute adsorption time
"A" = Difference in absorbance at 3365 $cm^{-1}$ in Air and under purge.
"B" = Difference in absorbance at 3365 $cm^{-1}$ for corresponding blank run.
"C" = "A" – "B"

Data in Table 1C demonstrates the ability of the associative PECs of the present invention to sequester atmospheric moisture when present as a deposited layer on a substrate. The FT-IR spectra of the adsorbed layers formed on the IRE by exposing it to solutions containing associative PECs can also be used to determine the relative amounts of the polymers present in a layer.

In all of the FT-IR experiments, use of the specified optical accessory allows visual inspection of the IRE surface, which permits an assessment of whether the surface bears a visible residue or not. The associative PECs of the present invention are useful for the modification of surfaces without the formation of visible residues, because the adsorbed layers formed by the associative PECs are so thin (<500 nm), and are not macroscopic films, as are commonly formed from coatings or polishes, and cannot be seen by the unaided human eye when present on treated surfaces.

Example 2

The size of the stable associative PECs, and the composition of the thin adsorbed layers formed by treating surfaces with aqueous solutions of PECs can be controlled by changing the ratio of the polymers comprising the associative PECs, i.e., by changing the R parameter.

The FT-IR spectrum of chitosan, PAA and citric acid all exhibit one or more unique absorbance bands allowing their presence, as well as relative amount present on the surface of the IRE to be detected and monitored in real time.

The data in Table 2 illustrate that the composition of a layer can be controlled by varying the R parameter of the associative PECs. Since there were no added surfactants, the data also illustrate the surprising activity of the associative PECs solutions on a solid surface, even in the absence of a drying step and any "wetting" of the solid surface by surfactants.

Referring to Table 2, in one experiment with the R=0.25 associative PEC solution, the adsorption time was 5 minutes, and the layer was rinsed 10 times, yielding the band intensities listed (sample CPAA1, layer analysis A being denoted as "CPAA1-A", for example). A second treatment of the IRE was then done (exposure #2) with the adsorbed layer in place, followed by 10 and then 50 total rinses. The relatively small increase in the amount of chitosan and PAA caused by the second exposure, seen comparing examples CPAA1-A and CPAA1-B, shows that adsorption onto the surface was nearly complete in the first 5 minute exposure, i.e. that the formation of a layer formed from the associative PEC solutions is desirably rapid, and that the layer is very substantive, since in the second exposure there was no net loss, but in fact a net gain in the amounts of both chitosan and PAA on the surface. The associative PEC layer was also very substantive, as indicated by the relatively small change in band intensities caused by additional rinsing (compare CPAA1-B and CPAA1-C). In another experiment with the R=0.25 associative PEC solution, the adsorption time was increased to 30 minutes, but the relative amounts of chitosan and PAA initially adsorbed are very similar to that achieved with two exposures of shorter time, as seen by comparing CPAA 1-D and CPAA 1-E with CPAA 1-B and CPAA 1-C, respectively. These data show that layer formation from the associative PECs formulations is "self-limiting", i.e., the average thickness of the adsorbed layers (directly proportional to the absorbance intensities, since the area of the IRE is the same and fixed in all experiments) does not grow to macroscopic dimensions which would otherwise become visible to the eye, instead appearing to be self-limiting and maintaining a film of less than 500 nm thickness. In addition, 50 additional rinses, for a total of 100 rinses, was done with the layer formed in the third experiment. The band intensities show only a very slight decrease in the band intensities of both polymers, i.e., the layers are very substantive, as seen by comparing CPAA 1-E with CPAA 1-F. After 50 rinses, all citric acid was eventually rinsed away, indicating utility of the PECs films to release actives over time.

Also discovered is that treatment of the surface with associative PECs with R<1, which are relatively rich in PAA, and with R>1, which are relatively rich in chitosan, both result in layers with more chitosan with more substantivity than the control solution of chitosan alone, enabling the control of the layer composition by using treatment solutions with selected R values. In the absence of the associative PECs, PAA alone does not absorb onto the surface.

The band intensity ratios in Table 2 show that the composition of the layers provided by the solutions of the associative PECs can be controlled by changing the R value. As the R value increases, the relative amount of chitosan in the layers also increases. Thus, the band intensity ratio is found to be 1.1291 for formulation CPAA1-C (R=0.25), and is found to be 3.6038 for formulation CPAA10-B (R=4.0).

TABLE 2

Chitosan/Alcosperse 465 PAA PECs

| Formulation # | R | Adsorption Time (min) | Number of Rinses | Chitosan C—O band absorbance (mAU) | PAA C=O band absorbance (mAU) | Band Intensity Ratio Chitosan C—O/PAA C=O |
|---|---|---|---|---|---|---|
| CPAA1 - A | 0.25 | 5 | 10 | 2.94 | 2.567 | 1.1453 |
| CPAA1 - B | 0.25 | 5 (2) | 10 | 3.45 | 3.488 | 0.9891 |
| CPAA1 - C | 0.25 | — | 50 | 3.227 | 2.858 | 1.1291 |
| CPAA1 - D | 0.25 | 30 | 10 | 3.216 | 3.315 | 0.9701 |
| CPAA1 - E | 0.25 | — | 50 | 3.11 | 2.83 | 1.0989 |
| CPAA1 - F | 0.25 | — | 100 | 3.073 | 2.606 | 1.1792 |
| CPAA2 - A | 0.50 | 5 | 10 | 2.819 | 1.898 | 1.4852 |
| CPAA2 - B | 0.50 | — | 50 | 2.819 | 1.704 | 1.6543 |
| CPAA2 - C | 0.50 | 30 | 10 | 2.991 | 2.609 | 1.1464 |
| CPAA2 - D | 0.50 | — | 50 | 2.881 | 2.443 | 1.1793 |
| CPAA3 - A | 0.75 | 5 | 10 | 2.847 | 1.509 | 1.8867 |
| CPAA3 - B | 0.75 | — | 50 | 2.859 | 1.378 | 2.0747 |
| CPAA4 - A | 1.0 | 5 | 10 | 2.798 | 1.357 | 2.0619 |
| CPAA4 - B | 1.0 | — | 50 | 2.781 | 1.171 | 2.3749 |
| CPAA4 - C | 1.0 | 5 | 10 | 2.813 | 1.37 | 2.0533 |
| CPAA4 - D | 1.0 | — | 50 | 2.77 | 1.225 | 2.2612 |
| CPAA5 - A | 1.26 | 5 | 10 | 2.902 | 1.334 | 2.1754 |
| CPAA5 - B | 1.26 | — | 50 | 2.94 | 1.041 | 2.8242 |
| CPAA6 - A | 1.49 | 5 | 10 | 2.595 | 1.122 | 2.3128 |
| CPAA6 - B | 1.49 | — | 50 | 2.629 | 0.976 | 2.6936 |
| CPAA7 - A | 1.76 | 5 | 10 | 2.605 | 1.036 | 2.5145 |
| CPAA7 - B | 1.76 | — | 50 | 2.603 | 0.873 | 2.9817 |
| CPAA8 - A | 2.01 | 5 | 10 | 2.595 | 1.028 | 2.5243 |
| CPAA8 - B | 2.01 | — | 50 | 2.564 | 0.827 | 3.1004 |
| CPAA9 - A | 3.0 | 5 | 10 | 2.173 | 0.739 | 2.9405 |
| CPAA9 - B | 3.0 | — | 50 | 2.08 | 0.608 | 3.4211 |
| CPAA10 - A | 4.0 | 5 | 10 | 2.278 | 0.766 | 2.9739 |
| CPAA10 - B | 4.0 | — | 50 | 2.292 | 0.636 | 3.6038 |
| C1-A Chitosan control (1) | — | 5 | 10 | 1.812 | 0.497 | 3.6459 |
| C1-B Chitosan control (1) | — | — | 50 | 1.794 | 0.198 | 9.0606 |

(1) Concentration of chitosan was 1.3 mM
(2) Additional exposure time of 5 minutes Example 3

The associative PECs of the present invention, when made with polymers that exhibit chemical stability to oxidants such as sodium hypochlorite or hydrogen peroxide, are useful for providing hydrophilic modification of surfaces through the use of cleaning products familiar to consumers.

Hypochlorite-stable associative PECs can be made from mixtures of the alkali metal salt of poly(acrylic acid) (PAA) and poly(diallyl dimethyl ammonium chloride) denoted as poly(DADMAC) or simply DADMAC. However, the surface of a Ge IRE suitable for the FT-IR experiments is changed by exposure to sodium hypochlorite, which is a relatively strong oxidant. Thus, the formulations cited in Tables 3.1 and 3.2 below, which are used to demonstrate associative PEC stability and substantivity, were formulated using sodium chloride as a substitute for the sodium hypochlorite. It is believed, without being bound by theory, that the difference between the chloride and hypochlorite salts is immaterial, both being electrolytes, to the behavior of the associative PECs in terms of the delivery of adsorbed layers. Independently, stability of the oxidant containing PECs compositions confirmed stability of both the bleach and PEC component polymers after prolonged storage.

TABLE 3.1

DADMAC/PAA PECs

| Formulation # | PAA (mM) (1) | DADMAC (mM) (2) | R | Surfactant (wt %) (3) | NaCl (wt %) (4) | Total concentration charged groups (mM) | Evaluation |
|---|---|---|---|---|---|---|---|
| 3DAD/PAA 2 | 0.558 | 0.116 | 0.207 | — | 0.1201 | 0.674 | Stable |
| 3DAD/PAA 3 | 0.580 | 0.225 | 0.387 | — | 0.1132 | 0.804 | Stable |
| 3DAD/PAA 4 | 0.565 | 0.325 | 0.575 | — | 0.1145 | 0.891 | Stable |
| 3DAD/PAA 5 | 0.577 | 0.424 | 0.735 | — | 0.1169 | 1.001 | Stable |
| 3DAD/PAA 9 | 0.567 | 0.859 | 1.515 | — | 0.1261 | 1.426 | Stable |
| 3DAD/PAA 12 | 0.549 | 1.177 | 2.144 | — | 0.1257 | 1.726 | Stable |
| 6DAD/PAA 2 | 0.549 | 0.108 | 0.197 | 0.0254 | 0.1208 | 0.657 | Stable |
| 6DAD/PAA 3 | 0.530 | 0.226 | 0.427 | 0.0243 | 0.1116 | 0.757 | Stable |

TABLE 3.1-continued

DADMAC/PAA PECs

| Formulation # | PAA (mM) (1) | DADMAC (mM) (2) | R | Surfactant (wt %) (3) | NaCl (wt %) (4) | Total concentration charged groups (mM) | Evaluation |
|---|---|---|---|---|---|---|---|
| 5DAD/PAA 2 | 0.541 | 0.117 | 0.217 | 0.0509 | 0.1522 | 0.658 | Stable |
| 5DAD/PAA 4 | 0.537 | 0.329 | 0.612 | 0.0508 | 0.1226 | 0.866 | Stable |
| 5DAD/PAA 5 | 0.534 | 0.449 | 0.842 | 0.0494 | 0.1266 | 0.983 | Stable |
| 5DAD/PAA 8 | 0.527 | 0.757 | 1.437 | 0.0520 | 0.1229 | 1.283 | Stable |
| 5DAD/PAA 9 | 0.530 | 0.855 | 1.615 | 0.0505 | 0.1323 | 1.385 | Stable |
| 5DAD/PAA 12 | 0.529 | 1.161 | 2.196 | 0.0504 | 0.1154 | 1.690 | Stable |
| 2DAD/PAA 2 | 0.603 | 0.106 | 0.175 | 0.3040 | 0.1365 | 0.709 | Stable |
| 2DAD/PAA 4 | 0.571 | 0.321 | 0.562 | 0.3047 | 0.1319 | 0.891 | Stable |
| 2DAD/PAA 5 | 0.569 | 0.417 | 0.732 | 0.3046 | 0.1232 | 0.986 | Stable |
| 2DAD/PAA 8 | 0.562 | 0.728 | 1.296 | 0.3077 | 0.1512 | 1.289 | Stable |
| 2DAD/PAA 10 | 0.552 | 0.985 | 1.784 | 0.3102 | 0.1525 | 1.538 | Stable |
| 2DAD/PAA 12 | 0.557 | 1.182 | 2.122 | 0.3065 | 0.1543 | 1.740 | Stable |
| 7DAD/PAA 2 | 0.541 | 0.120 | 0.222 | 0.8964 | 0.1194 | 0.661 | Stable |
| 7DAD/PAA 4 | 0.645 | 0.326 | 0.506 | 0.8890 | 0.1154 | 0.971 | Stable |
| 7DAD/PAA 5 | 0.551 | 0.435 | 0.789 | 0.9010 | 0.1143 | 0.986 | Stable |
| 7DAD/PAA 12 | 0.535 | 1.161 | 2.170 | 0.9017 | 0.1115 | 1.697 | Stable |

(1) Poly(DADMAC) from Aldrich, batch 02319JC, average MW of $2.5 \times 10^5$ Daltons, final dilution to 0.1661 wt % (about 10.3 mM cationic groups), pH 12
(2) Aquatreat AR-4, 0.0774 wt % (about 10.9 mM anionic carboxylate groups), pH 12.
(3) 20 wt % sodium chloride pH 12.0.
(4) 3 wt % Amine oxide, Ammonyx LO (Stepan Corp.), pH 12.

TABLE 3.2

DADMAC/PAA PECs

| Formulation # | PAA (mM) (1) | DADMAC (mM) (2) | R | Surfactant (wt %) (3) | NaCl (wt %) (4) | Total concentration charged groups (mM) | Evaluation |
|---|---|---|---|---|---|---|---|
| 8DAD/PAA 2 | 0.557 | 0.118 | 0.211 | — | 0.1195 | 0.675 | stable |
| 8DAD/PAA 3 | 0.559 | 0.220 | 0.394 | — | 0.1195 | 0.779 | stable |
| 8DAD/PAA 4 | 0.553 | 0.333 | 0.602 | — | 0.1210 | 0.886 | stable |
| 8DAD/PAA 5 | 0.574 | 0.429 | 0.747 | — | 0.1193 | 1.002 | stable |
| 8DAD/PAA 6 | 0.595 | 0.537 | 0.904 | — | 0.1205 | 1.132 | stable |
| 8DAD/PAA 11 | 0.561 | 1.080 | 1.926 | — | 0.1190 | 1.641 | stable |
| 8DAD/PAA 12 | 0.559 | 1.160 | 2.074 | — | 0.1189 | 1.719 | stable |
| 9DAD/PAA 2 | 0.561 | 0.218 | 0.388 | 0.0235 | 0.1194 | 0.779 | stable |
| 9DAD/PAA 3 | 0.557 | 0.105 | 0.188 | 0.0236 | 0.1196 | 0.662 | stable |
| 9DAD/PAA 4 | 0.553 | 0.218 | 0.394 | 0.0231 | 0.1199 | 0.771 | stable |
| 9DAD/PAA 5 | 0.595 | 0.308 | 0.518 | 0.0232 | 0.1191 | 0.903 | stable |
| 9DAD/PAA 6 | 0.576 | 0.410 | 0.711 | 0.0235 | 0.1197 | 0.986 | stable |
| 9DAD/PAA 7 | 0.553 | 0.527 | 0.953 | 0.0237 | 0.1197 | 1.080 | stable |
| 10DAD/PAA 3 | 0.561 | 0.211 | 0.376 | 0.0494 | 0.1211 | 0.772 | stable |
| 10DAD/PAA 4 | 0.553 | 0.321 | 0.580 | 0.0485 | 0.1254 | 0.874 | stable |
| 10DAD/PAA 5 | 0.562 | 0.415 | 0.738 | 0.0484 | 0.1294 | 0.977 | stable |
| 10DAD/PAA 11 | 0.563 | 0.998 | 1.772 | 0.0480 | 0.1164 | 1.561 | stable |
| 10DAD/PAA 12 | 0.565 | 1.124 | 1.991 | 0.0483 | 0.1175 | 1.689 | stable |
| 11DAD/PAA 2 | 0.551 | 0.102 | 0.186 | 0.8990 | 0.1207 | 0.654 | stable |
| 11DAD/PAA 3 | 0.558 | 0.199 | 0.357 | 0.8994 | 0.1273 | 0.757 | stable |
| 11DAD/PAA 4 | 0.549 | 0.319 | 0.581 | 0.8970 | 0.1170 | 0.869 | stable |
| 11DAD/PAA 5 | 0.547 | 0.409 | 0.747 | 0.9008 | 0.1207 | 0.956 | stable |
| 11DAD/PAA 6 | 0.550 | 0.519 | 0.944 | 0.9007 | 0.1205 | 1.068 | stable |

(1) Poly(DADMAC) from Aldrich,, batch 05525PB average MW of 1.0 to $2.0 \times 10^5$ Daltons, pH 12, diluted to 0.1701 wt % (about 10.56 mM cationic groups).
(2) Aquatreat AR-7H poly(acrylic acid) from Alco Chemical, average MW of $8.72 \times 10^5$ Daltons, pH 12, diluted to 0.0780 wt % (about 10.99 mM anionic carboxylate groups).
(3) 20 wt % sodium chloride, pH 12.
(4) 3.0 wt % Amine oxide, Ammonyx LO (Stepan Corp.), pH 12.

Table 3.2 evaluates formulations without and with hypochlorite-stable surfactant with associative PECs made using low molecular weight poly(DADMAC) and higher molecular weight PAA. The formulations were made in the same way as those described in Table 3.1.

The compositions in Tables 3.1 and 3.2 illustrate that stable DADMAC/PAA associative PECs can be assembled over a wide range of R values, over a wide range of surfactant concentrations useful in the control of the surface wetting and cleaning properties of the formulations, and in the presence of significant concentrations of an electrolyte. In contrast to the known art, when the associative PECs are assembled in the manner described herein, stable systems can be produced without particular regard to the relative molecular weights of the polymers comprising the associative PECs. Table 3.3 reports FT-IR band intensities in spectra of adsorbed layers formed by exposure of Ge IRE to solutions containing, associative PECs described in Table 3.1 for 5 minutes, followed by immediate rinsing. Spectra were obtained under dry nitrogen purge.

Multiple exposures of the Ge surface were made using the inventive compositions for 5 minutes, followed by rinsing the surface 20 times with water, and then the spectra were recorded. This adsorbed layer was then exposed to the indicated associative PEC solution again, followed by rinsing, and a spectrum recorded for "exposure 2". A third exposure was done in the same way. The small increase in the amounts of DADMAC and PAA caused by the second and third exposures shows that adsorption onto the surface was nearly complete in the first 5 minute exposure, i.e. that the formation of the adsorbed layers formed from the associative PEC solutions is fairly rapid, and that while the adsorbed layers are very substantive, they nevertheless tend to self-equilibrate and maintain a favorably thin invisible layer on a treated surface, rather than building up to undesirable macroscopic (and hence visible) layers Polymer PAA, which becomes negatively charged at pH 12, as in the examples in Tables 3.1, 3.2 and 3.3, does not adsorb onto the Ge surface, which is also slightly negatively charged. However, PAA is clearly present in the adsorbed layers when delivered via treatment using the inventive associative PEC solutions.

TABLE 3.3

| Formulation # | PAA Carboxylate (mAU) | DADMAC $CH_3$ (mAU) | R | Treatment (2) Number of Rinses |
|---|---|---|---|---|
| 3DAD/PAA 4 | 0.531 | 0.557 | 0.5752 | 20 |
| 3DAD/PAA 5 | 1.066 | 0.692 | 0.7349 | 20 |
| 3DAD/PAA 8 | 2.702 | 1.045 | 1.3072 | 20 |
| 3DAD/PAA 4 | 0.686 | 0.568 | 0.5752 | 20 |
| 3DAD/PAA 4 | 1.045 | 0.671 | 0.5752 | 40 |
| 3DAD/PAA 4 | 1.166 | 0.721 | 0.5752 | 60 |
| Control (1) | 0.078 | 0.57 | N/A | 20 |

(1) DADMAC polymer only at 10.0 mM concentration in sodium chloride solution.
(2) Exposed to formulation indicated for 5 minutes with no separate drying step, followed by number of rinses indicated.

Example 4

The following example demonstrates surface modification using DADMAC/PAA associative PECs in treatment compositions having a hypochlorite-stable surfactant. FT-IR was used to determine the formation of adsorbed layers from associative PEC solutions containing various amounts of a relatively oxidant-stable surfactant, Ammonyx LO. These illustrative compositions are suitable as ready-to-use treatment compositions.

TABLE 4.1

| Formulation # | PAA Carboxylate (mAU) | DADMAC $CH_3$ (mAU) | R |
|---|---|---|---|
| 7DAD/PAA 2 | 0.295 | 0.509 | 0.222 |
| 7DAD/PAA 3 | 0.407 | 0.474 | 0.308 |
| 7DAD/PAA 4 | 0.687 | 0.582 | 0.506 |
| 7DAD/PAA 5 | 0.985 | 0.659 | 0.789 |
| 7DAD/PAA 6 | 0.085 | 0.276 | 0.988 |
| 7DAD/PAA 7 | 1.295 | 0.738 | 1.191 |
| 7DAD/PAA 8 | 2.753 | 1.016 | 1.389 |
| 7DAD/PAA 9 | 1.858 | 0.94 | 1.597 |
| 7DAD/PAA 10 | 1.99 | 0.898 | 1.756 |
| 7DAD/PAA 11 | 1.31 | 0.817 | 1.974 |

In Table 4.1, the Ge IRE surface was treated with the indicated compositions for 5 minutes, followed by 20 rinses with water without a drying step, the spectra obtained under a dry nitrogen purge. Results show that the adsorbed associative PECs layers are formed rapidly, even in the absence of a drying step, and even in the presence of surfactant, both PAA and DADMAC being confirmed as present in the adsorbed layers.

TABLE 4.2

| Formulation # | PAA Carboxylate (mAU) | DADMAC $CH_3$ (mAU) | R (1) |
|---|---|---|---|
| 7DAD/PAA 2 | 0.562 | 0.581 | 0.222 |
| 7DAD/PAA 3 | 0.892 | 0.596 | 0.308 |
| 7DAD/PAA 4 | 2.662 | 0.985 | 0.506 |
| 7DAD/PAA 5 | 2.422 | 0.94 | 0.789 |
| 7DAD/PAA 6 | 0.178 | 0.319 | 0.988 |
| 7DAD/PAA 7 | 1.084 | 0.75 | 1.191 |
| 7DAD/PAA 8 | 5.089 | 1.454 | 1.389 |
| 7DAD/PAA 9 | 5.247 | 1.565 | 1.597 |
| 7DAD/PAA 10 | 5.441 | 1.583 | 1.756 |
| 7DAD/PAA 11 | 3.034 | 1.156 | 1.974 |

(1) FT-IR band intensities in the spectra of adsorbed layers formed by drying 10 microliters of formulations containing DADMAC/PAA PECs and 0.89% Ammonyx LO on the IRE surface, followed by 20 rinses with water. Spectra of layers obtained under dry nitrogen purge.

Table 4.2 represents results of surface modification with DADMAC/PAA PECs utilizing a drying step following treatment. Here results indicate that, even in the presence of significant amounts of surfactant, substantive adsorbed layers are formed from the formulations containing the associative PECs, and the total amount of adsorbed polymers is increased somewhat. Without being bound by theory, it is believed that the drying step immediately following treatment enables rearrangement of the PECs on the surface, likely resulting in a denser layer and/or denser array of the associative PECs at the surface.

Several additional DADMAC/PAA PECs were evaluated, reversing the relative molecular weights of the polymers used. The data in Table 4.3 show that adsorbed layers from these systems are also produced in the presence of surfactant and a drying step, despite extensive rinsing with water. Control of the stability of the associative PECs through selection of appropriate R values, which controls the composition and size of the associative PECs, can be achieved with a range of polymers of the same chemical type, but varying in molecular weight.

TABLE 4.3

| Formulation # | PAA Carboxylate (mAU) (1) | DADMAC $CH_3$ (mAU) (1) | R |
|---|---|---|---|
| 11DAD/PAA 2 | 0.097 | 0.258 | 0.186 |
| 11DAD/PAA 3 | 0.282 | 0.446 | 0.357 |
| 11DAD/PAA 4 | 0.551 | 0.488 | 0.581 |

TABLE 4.3-continued

| Formulation # | PAA Carboxylate (mAU) (1) | DADMAC $CH_3$ (mAU) (1) | R |
|---|---|---|---|
| 11DAD/PAA 5 | 0.853 | 0.622 | 0.747 |
| 11DAD/PAA 6 | 2.081 | 0.781 | 0.943 |

(1) FT-IR band intensities in the spectra of adsorbed layers formed by drying 10 microliters of formulations containing DADMAC/PAA PECs and 0.89 wt % Ammonyx LO on the IRE surface, followed by 20 rinses with water. Spectra of layers obtained under dry nitrogen purge. The systems were all found to be stable.

Example 5

Results in Table 5 show that the relative amounts of water taken up by the thin adsorbed layers of DADMAC/PAA PECs from Example 4 following various application, drying and rinsing steps.

TABLE 5

| Formulation # | "A" PAA Carboxylate (mAU) | "B" DADMAC $CH_3$ (mAU) | "C" Water uptake in PEC layer (mAU) (1) | R | Treatments (2) |
|---|---|---|---|---|---|
| 7DAD/PAA 5 | 0.696 | 0.689 | 0.30 | 0.789 | No dry step Rinsed |
| 7DAD/PAA 5 | 1.71 | 0.949 | 1.16 | 0.789 | Dried Rinsed |
| 7DAD/PAA 11 | 1.244 | 0.929 | 0.92 | 1.974 | No dry step Rinsed |
| 7DAD/PAA 11 | 2.735 | 1.277 | 2.087 | 1.974 | Dried Rinsed |
| 7DAD/PAA 12 | 1.327 | 0.911 | 0.871 | 2.17 | No dry step Rinsed |
| 7DAD/PAA 12 | 2.955 | 1.351 | 2.409 | 2.17 | Dried Rinsed |

(1) "C" = "B" − "A"
(2) "No dry step" means 5 minute exposure to formulation containing associative PECs, followed by 20 rinses with water. "Dried" means 10 microliters of formulation was spread on IRE, allowed to dry, and then rinsed 20 times with water.

Table 5 results demonstrate that more water is taken up at the surface in the presence of the adsorbed layers, compared to the untreated Ge surface, and that the amount of water present increases as the amount of associative PECs (total polymer) on the surface increases. Thus, hydrophilic thin adsorbed layers can be produced from formulations containing oxidant-stable associative PECs.

Example 6

The following examples demonstrate hypochlorite stability in treatment compositions containing DADMAC/PAA PECs, which all show acceptable stability against precipitation and degradation by the optional bleach component being present.

TABLE 6.1

| Sample # | R (1) | Surfactant (wt %) (2) | Salt (wt %) (3) | Buffer Type (3) | Initial Hypochlorite (wt %) (4) | % of Hypochlorite Remaining (5) |
|---|---|---|---|---|---|---|
| A1 | 0.25 | 0 | 0.016 | $Na_2O \cdot SiO2$ | 0.020 | 89 |
| A2 | 0.50 | 0 | 0.016 | $Na_2O \cdot SiO_2$ | 0.020 | 72 |
| A3 | 0.50 | 0 | 0.022 | $K_2CO_3$ | 0.025 | 83 |
| A4 | 0.25 | 0.005 | 0.021 | $K_2CO_3$ | 0.025 | 81 |
| A5 | 0.50 | 0.005 | 0.021 | $K_2CO_3$ | 0.025 | 83 |
| A6 | 0.05 | 0.02 | 0.022 | $K_2CO_3$ | 0.027 | 79 |
| A7 | 0.30 | 0.02 | 0.021 | $K_2CO_3$ | 0.026 | 76 |
| A8 | 0.05 | 0.02 | 0.41 | $K_2CO_3$ | 0.500 | 88 |

TABLE 6.1-continued

| Sample # | R (1) | Surfactant (wt %) (2) | Salt (wt %) (3) | Buffer Type (3) | Initial Hypochlorite (wt %) (4) | % of Hypochlorite Remaining (5) |
|---|---|---|---|---|---|---|
| A9 | 0.30 | 0.02 | 0.41 | $K_2CO_3$ | 0.500 | 80 |
| A10 | 0.05 | 0.02 | 1.65 | $K_2CO_3$ | 2.00 | 84 |
| A11 | 0.30 | 0.02 | 1.64 | $K_2CO_3$ | 2.00 | 83 |

(1) PAA = Aquatreat AR-4 ™, the total combined final polymer concentration being 1.5 mM in all formulations.
(2) Ammonyx LO ™ available from the Stepan Co.
(3) Sodium chloride, sodium silicate, sodium hydroxide, potassium carbonate were J. T. Baker reagent grade.
(4) Sodium hypochlorite (Clorox ™ Regular Bleach, 6.7-6.9 wt % hypochlorite assayed)
(5) After 4 weeks at 120° F. All samples remained clear and free of precipitates.

Formulations A1 through A3 illustrate useful embodiments of the present invention suitable for us as daily after shower treatment compositions that provide hydrophilic modification of surfaces via the adsorption of the DADMAC/PAA PECs, and daily germ reduction employing relatively low hypochlorite levels. Formulations A4 and A5 are embodiments useful as ready-to-use treatment compositions that provide hydrophilic modification of hard surfaces, including sink basins, toilet exteriors, floors, and countertops, also providing cleaning due to the incorporation of surfactant, and germ and mildew reduction due to the hypochlorite present. Formulations A6 through A11 further illustrate embodiments stable at higher ionic strengths and elevated surfactant levels, and demonstrate chemical stability of sodium hypochlorite in the presence of associative PECs with or without the presence of common bleach stable surfactants available for commercial usage.

TABLE 6.2

| Sample # | R (1) | Surfactant (wt %) (2) | Starting HOOH (wt %) | % HOOH remaining (3) |
|---|---|---|---|---|
| B1 | 20 | 0.02 | 1.11 | 84 |
| B2 | 3.3 | 0.02 | 1.08 | 85 |
| B3 | 20 | 0.10 | 1.08 | 92 |
| B4 | 3.3 | 0.10 | 1.10 | 94 |
| B5 | 20 | 0.02 | 2.13 | 86 |
| B6 | 3.3 | 0.02 | 2.13 | 87 |
| B7 | 20 | 0.1 | 2.13 | 91 |
| B8 | 3.3 | 0.1 | 2.14 | 93 |
| B9 | 20 | 0.02 | 4.21 | 85 |
| B10 | 3.3 | 0.02 | 4.19 | 87 |
| B11 | 20 | 0.1 | 4.27 | 91 |
| B12 | 3.3 | 0.1 | 4.25 | 92 |

(1) Total concentration of charged groups from polymers 1.5 mM, pH 2-3, stored at 120° F. for 4 weeks.
(2) 3 wt % final Ammonyx LO surfactant, added after PEC formation, being charged at formulation pH.
(3) All samples remained clear without precipitate.

Example 7

Formulations shown in Tables 7.1 and 7.2 demonstrate that thin, invisible adsorbed layers can be formed by exposing the surface to be modified to bleach tolerant formulations of stable associative PECs formed from R values of <1.0 and >1.0. FT-IR band intensities were measured in the spectra of adsorbed layers formed by drying 10 microliters of formulations shown in Table 7.1 of DADMAC/Alcosperse 747 PECs on an Ge IRE surface, followed by 20 rinses with water, followed by dry nitrogen purge.

TABLE 7.1

| Formulation # | Alcosperse 747 (wt %) | DADMAC (wt %) | Acid group molarity (mM) | DADMAC quaternary group molarity (mM) | R | NaCl (wt %) | Ammonyx LO (wt %) | Total concentration charged groups (mM), pH 12 | Comment |
|---|---|---|---|---|---|---|---|---|---|
| DAD747 1 | 0.0096 | 0.0053 | 0.55 | 0.33 | 0.6 | 0 | 0 | 0.88 | Stable Clear |
| DAD747 2 | 0.0096 | 0.0177 | 0.55 | 1.1 | 2.0 | 0 | 0 | 1.65 | Stable Clear |
| DAD747 3 | 0.0096 | 0.0177 | 0.55 | 1.1 | 2.0 | 0.22 | 0.90 | 1.65 | Stable Clear |

TABLE 7.2

| Formulation # | Alcosperse 747 Carboxylate (mAU)(1,2) | DADMAC $CH_3$ (mAU)(2) | R |
|---|---|---|---|
| DAD747 1 | 4.154 | 1.266 | 0.6 |
| DAD747 2 | 3.47 | 1.246 | 2 |
| DAD747 3 | 3.097 | 1.356 | 2 |

(1)Alcosperse 747 carboxylate band around 1565 $cm^{-1}$
(2)Measurements taken after 20 water rinses, under dry nitrogen purge

TABLE 7.3

| Formulation # | "C" Water uptake in PEC layer (mAU) | R |
|---|---|---|
| DAD747 1 | 1.31 | 0.6 |
| DAD747 3 | 1.70 | 2 |
| DAD747 2 | 1.73 | 2 |

Table 7.3 shows results of FT-IR analysis of the water uptake of the compositions of Table 7.1, demonstrating that hydrophilic thin layers can be produced from formulations containing these oxidant-stable associative PECs. By controlling the composition of the associative PECs and the exposure conditions, hydrophilic modification of surfaces can be accomplished in one embodiment of the present invention by using treatment compositions that can contain oxidants for simultaneous disinfection and cleaning of surfaces to which the inventive compositions are applied.

Example 8

The associative PECs of the present invention can be used to incorporate antimicrobial molecules into the thin, invisible layers formed on a variety of surfaces exposed to treatment compositions, exhibiting enhanced substantivity of the biocides when they are incorporated into the PECs layers, thus being available to reduce or eliminate germs on surfaces that are subjected even to extensive rinsing with water, or exposure to high humidity, bodily fluids, etc.

When formulating associative PECs compositions that are to contain a charged surfactant or cationic biocide, or a mixture of a charged surfactant or biocide and uncharged surfactant, for example, it is preferred to first assemble the associative PECs according to the methods of the present invention prior to introducing the charged adjuncts.

TABLE 8.1

| Formulation # | Glucopon 325N (wt %) | Barquat 4250Z (wt %) | Citric acid (wt %) | Total concentration charged groups (mM) | R |
|---|---|---|---|---|---|
| BIO1 (1) | 0.075 | 0.04 | 0.75 | 0 | — |
| BIO2 (1) | 0 | 0.50 | 0 | 0 | — |
| CPAA 11 | 0.0739 | 0 | 0.75 | 1.32 | 0.25 |
| CPAA 12 | 0.0739 | 0.0394 | 0.75 | 1.32 | 0.25 |
| CPAA 13 | 0.0737 | 0.0393 | 0.75 | 1.34 | 0.50 |
| CPAA 14 | 0.0737 | 0.0393 | 0.75 | 1.35 | 1.0 |
| CPAA 15 | 0.0713 | 0.0381 | 0.75 | 1.30 | 1.5 |
| CPAA 16 | 0.0737 | 0.0393 | 0.75 | 1.35 | 4.0 |

(1) Controls with No PECs present. NA = Not Applicable.

TABLE 8

| Formulation # | R | Federal Labs Chitosan Stock A (mL) (1) | Alcosperse 465 PAA. Stock B (mL) (2) | 10 wt % Citric Acid (mL) (3) | H₂O (mL) | Glucopon 325N stock (mL) | Glucopon 325N/Barquat 4250Z stock (mL) | Total concentration Charged groups (mM) |
|---|---|---|---|---|---|---|---|---|
| CPAA 11 | 0.25 | 7.2 | 9.7 | 20.6 | 258 | 10 | 0 | 1.32 |
| CPAA 12 | 0.25 | 7.2 | 9.7 | 20.6 | 258 | 0 | 10.0 | 1.32 |
| CPAA 13 | 0.5 | 12 | 8.23 | 18.5 | 257.60 | 0 | 10.0 | 1.34 |
| CPAA 14 | 1.00 | 18.14 | 6.23 | 15.85 | 256.14 | 0 | 10.0 | 1.35 |
| CPAA 15 | 1.5 | 21.76 | 4.98 | 14.2 | 265.4 | 0 | 10.0 | 1.30 |
| CPAA 16 | 4 | 29.0 | 2.49 | 11.02 | 253.75 | 0 | 10.0 | 1.35 |

(1) Chitosan stock 2.35 mg/mL, diluted into citric acid solution, order of addition as required for given R value.
(2) PAA stock 2.00 mg/mL, diluted into citric acid solution
(3) Providing final 0.75 wt % citric acid at pH 2.2.

To demonstrate that formulations described in Table 8 containing quaternary ammonium biocide and nonionic surfactant are useful for cleaning and disinfecting surfaces, 10 microliters of each formulation was applied to the Ge surface of the IRE and allowed to dry, followed by 50 rinses with water, dried under dry nitrogen purge and then the spectra obtained with results shown in Table 8.1 below.

Measurement of the quaternary ammonium biocide ("Quat") absorbance band near 2926 $cm^{-1}$ confirms it being present in the invisible PECs layers formed on the surface after treatment, despite the high number of subsequent water rinses. In contrast, monitoring of the absorbance bands attributed to the polysaccharide surfactant (APG) showed that this neutral surfactant was completely rinsed away.

TABLE 8.2

Chitosan/PAA PECS exhibiting controlled quaternary biocide retention

| Formulation # | # Rinses (1) | CH₂ Total Quat (mAU) | "A" PAA C=O band, (mAU) | "B" Chitosan C—O band (mAU) | "C" Water uptake in PEC layer (mAU) (2) | Quat presence confirmed |
|---|---|---|---|---|---|---|
| BIO1 | 10 | 2.328 | 0.439 | 0.395 | −0.38 | Y |
| BIO2 | 50 | 1.555 | 0.288 | 0.435 | 0.05 | Y |
| CPAA 11 | 50 | 0.455 | 1.311 | 2.821 | 1.799 | N (3) |
| CPAA 12 | 50 | 1.644 | 0.724 | 1.46 | 0.638 | Y |
| CPAA 13 | 50 | 1.082 | 0.597 | 1.827 | 0.563 | Y |
| CPAA 14 | 50 | 0.901 | 0.55 | 1.764 | 0.876 | Y |
| CPAA 15 | 50 | 0.833 | 0.4 | 1.923 | 0.883 | Y |
| CPAA 16 | 50 | 0.365 | 0.336 | 2.534 | 1.271 | N (3) |

(1) After surface treated with formulation
(2) "C" = "A" − "B"
(3) Absent or below detection limit The data in Table 8.2 demonstrate that thin, invisible layers incorporating chitosan, PAA and the quaternary ammonium biocide are formed that resist extensive rinsing with water. It is believed, without being bound by theory, that adsorption of the Barquat onto the surface increases the hydrophobicity (increases the water contact angle) due to nearly complete coverage of the surface and the orientation of the hydrophobic methylene chains of the Barquat molecules on the surface. The water uptake of the surface is significantly inhibited by the presence of the adsorbed Barquat. Accordingly, the composition and R value may be adjusted to provide the desired balance of hydrophilicity/hydrophobicity and the desired level of an antimicrobial present in the deposited associative PECs layers. This is further illustrated in Table 8.2 showing that adjustment of the R value of the associative PEC compositions can serve to change the amount of quaternary biocide present in deposited films. Alternatively, the data also show how adjusting the R value is useful in adjusting the relative amounts of chitosan and PAA present in the thin layers formed on surfaces, and illustrates that at selected R values (0.25, 4) the higher levels of chitosan present in the deposited associative PECs can be selected to control or prevent the retention of a similarly charged quaternary biocide in the deposited layers. The presence of Barquat anchored to the surface treated with CPAA 16 is not detected, compared to the case of the control sample BIO1, which does not contain PECs. Thus, composition CPAA 16 would be very useful in mitigating the loss of Barquat to anionic sites on the surfaces of nonwoven wipes, cloths, mops, etc.

Example 9

In this example the effects of multiple applications of the inventive formulations onto surfaces is illustrated using compositions shown in Table 9.1.

TABLE 9.1

Effect of multiple repeated treatments to surface

| Formulation # | "A" $CH_2$ Total Quat (mAU) | "B" PAA C=O band (mAU) | "C" Chitosan C—O band (mAU) | Water uptake in PEC layer (mAU) | R | Application (Stepwise) |
|---|---|---|---|---|---|---|
| BIO1 | 1.555 | 0.288 | 0.435 | 0.05 | — | 1 |
| CPAA 12 | 1.233 | 0.679 | 1.565 | 0.515 | 0.25 | 1 |
| CPAA 12 | 1.332 | 0.961 | 2.195 | 1.02 | 0.25 | 2 |
| CPAA 12 | 1.806 | 1.125 | 2.526 | 1.421 | 0.25 | 3 |
| CPAA 14 | 0.525 | 0.399 | 1.998 | 0.885 | 1.0 | 1 |
| CPAA 14 | 0.532 | 0.479 | 2.664 | 1.403 | 1.0 | 2 |
| CPAA 14 | 0.619 | 0.434 | 2.715 | 1.446 | 1.0 | 3 |

Table 9.1 shows that the relative amounts of Quat and both polymers on the surface increase with multiple stepwise applications of the inventive formulations, despite rinsing of the surfaces between applications, and multiple exposures to the surfactants also present in the formulations, demonstrating the durability of the associative PEC layers formed on the treated surface. Results also indicate that control of the amount of adsorbed Quat is possible through selected of a desired R value. The results also indicate that the water uptake of the layers desirably increases with multiple exposures, yielding both hydrophilic modification of the surface together with anchored biocide.

Example 10

In this example, the formation of an adsorbed layer of associative PECs onto a surface by employing a multi-step process is illustrated.

TABLE 10

Comparison of One and Two-Step Processes for Forming Associative PEC Layers with Anchored Quaternary Ammonium Biocide

| Formulation # | "A" $CH_2$ Total Quat (mAU) | "B" PAA C=O band (mAU) | "C" Chitosan C—O band (mAU) | Water uptake in PEC layer (mAU) | Application Step # and Treatment Detail (1) |
|---|---|---|---|---|---|
| BIO1 | 1.555 | 0.288 | 0.435 | 0.05 | Control (2) |
| CPAA 11 | 0.536 | 1.511 | 3.093 | 2.31 | Application 1 PECs without Quat |
| BIO1 | 1.117 | 1.23 | 2.644 | 1.783 | Application 2 Quat only |
| CPAA 11 | 0.994 | 2.352 | 4.034 | 2.613 | Application 3 PECs without Quat |
| BIO1 | 1.328 | 1.723 | 3.23 | 1.989 | Application 4 Quat only |
| CPAA 12 | 1.233 | 0.679 | 1.565 | 0.515 | Single Application PECs with Quat |

(1) All surfaces dried, then rinsed 50x with water after indicated application step using specified formulation.
(2) Quat alone, Barquat 4250Z (0.5 wt %) present at same level as in "CPAA" series associative PECs treatments.

Results in Table 10 demonstrate that the non-inventive treatment composition BIO1 results in the adsorption of some quaternary biocide on the surface, but does not significantly increase the water uptake of the surface, as indicated by the small "C" value. In contrast, treatment using inventive compositions with and without the quaternary ammonium biocide demonstrate the ability of the associative PECs formulations to not only increase the surface hydrophilicity (indicated by the increased water uptake) but to deposit and hold a much greater level of the Quat biocide with the invisible deposited PECs film on the treated surface. Surprisingly, once the associative PECs layer is formed on a treated surface, subsequent exposure to a biocide-only containing composition results in substantial uptake of the biocide into the PECs layer. Thus, the associative PECs may be employed in a two step process whereby an established PECs layer can be rendered antimicrobial by subsequent exposure to a biocide containing solution free of the associative PECs, without any significant removal of the originally deposited PECs layer.

These results demonstrate that the amount of quaternary ammonium biocide and the amount of deposited associative PECs on a treated surface can be renewed by individual applications of a biocide/surfactant formulation or an associative PECs treatment composition, with or without quaternary biocide present. Thus, embodiments in which cleaning of the surface is done first, followed by "touch up" applications of a cleaning and/or disinfecting product without the associative PECs present is possible as well. These compositions represent embodiments of the present invention in which associative PEC treatment of a surface may be alternated and/or combined with other surface treatment means.

Example 11

This example repeats similar treatment steps to Example 10 with the exception that the treated surfaces were not allowed to completely dry between individual treatment steps in order to illustrate the durability of the associative PECs.

TABLE 11

Anchoring of Quaternary Ammonium Biocide
With and Without PEC Layer

| Formulation # | "A" CH$_2$ Total Quat (mAU) | PAA C=O band (mAU) | "B" Chitosan C—O band (mAU) | "C" Water uptake in PEC layer (mAU) | Treatment (1) |
|---|---|---|---|---|---|
| BIO2 | 1.632 | 0.265 | 0.402 | 0.224 | Application 1 Biocide without PECs |
| BIO2 | 1.717 | 0.36 | 0.457 | 0.721 | Application 2 Biocide without PECs |
| BIO2 | 1.871 | 0.391 | 0.466 | 0.765 | Application 3 Biocide without PECs |
| CPAA11 | 0.668 | 1.86 | 2.679 | 1.636 | Application 1 PECs without biocide |
| BIO2 | 4.359 | 1.125 | 1.773 | 1.1 | Application 2 Biocide without PECs |
| BIO2 | 3.419 | 1.278 | 1.77 | 1.276 | Application 2 (2) Biocide without PECs |

(1) Surfaces rinsed 50× with water after indicated application step, without allowing time for indicated formulation application to dry on treated surface.
(2) Same as (1) but rinsed 100× with water.

The results in Table 11 show that more quaternary biocide is anchored onto the surface which has been first treated with the biocide-free associative PECs formulation than is anchored onto the surface which is initially clean, but which has not been treated with the associative PECs formulations. Surprisingly, even three successive treatments of the surface with a formulation having a relatively high concentration of the quaternary biocide alone does not result in as much anchored Quat biocide as a single, two-step treatment in which a layer of biocide-free associative PECs is established, followed by "loading" of the established associative PECs layer by subsequent application of the biocide only containing formulation (BIO2 formulation.). This illustrates utility of embodiments of the present invention employing a two step modification of a surface that would be applicable for use in cleaning a toilet bowl interior, for example. In one embodiment, the second treatment step could be used to introduce an antimicrobial agent after an initial cleaning step that establishes the associative PECs layers onto treated surfaces. In another embodiment of the present invention, the renewal of the quaternary ammonium biocide in an associative PECs layer can be accomplished by delivery, for example using a toilet rim hanger device or in-tank device, of a sufficient amount of quaternary ammonium biocide to the bowl with each flush.

Light Scattering Measurements of PECs Solutions

Light scattering techniques are used to characterize the absolute molecular weights as well as the size of the associative PECs of the present invention. Dynamic light scattering experiments are used to determine the hydrodynamic radii ($R_H$) of the associative PECs, while static light experiments are used to measure the absolute molecular weight (MW) and radii of gyration ($R_G$) of the associative PECs. Those skilled in the art recognize that $R_H$ and $R_G$ can have somewhat different absolute values, and that their ratio ($\rho=R_G/R_H$) can also provide information on the shape of the colloidal particles. Low values of $\rho$ are observed for particles that are spherical, intermediate values are found for particles which can dynamically assume shapes that are slightly elongated, while the higher values are observed for particles that are more rigid and formally rod-shaped in aqueous solutions.

The hydrodynamic radii ($R_H$) of the associative PECs of the present invention were obtained via dynamic light scattering experiments that employed a Wyatt DynaPro DLS detection system with a 50 mW laser (wavelength $\square$=830 nm). Fluctuations in light scattering intensities were obtained at 90° and autocorrelation functions were derived using DYNAMICS software provided by Wyatt Technology Corporation. All experiments were conducted under controlled temperature and humidity and a total of 100 acquisitions were collected for each sample. Prior to analysis by DLS, each associative PEG sample was centrifuged for one hour at 3750 rpm to remove dust.

Radii of gyration ($R_G$) and the weight-averaged MWs ($M_w$) of the associative PECs were measured by batch-mode static light scattering using a Wyatt DAWN-EOS multiangle laser light scattering (MALLS) detector (wavelength=690 nm). Prior to analysis, the system was calibrated at 90° with toluene and the other detectors were normalized using a 56 kDa PEO standard dissolved in a 0.7 wt % citric acid. Samples were centrifuged at 3750 rpm and immediately analyzed in custom-engineered light scattering cuvettes (Wilmad-Labglass). Debye plots were generated for each sample, which yielded both $R_G$ and $M_w$. All light scattering data was processed in ASTRA V software using either first or second-ordered fitting.

Example 12

Controlled Particle Size of Chitosan/PAA PECs

Results in Table 12 are presented from light scattering analysis of the associative PECs formulations described in Table 1B.

TABLE 12

Molecular Weights and Radii of Stable Chitosan/PAA
PECs Determined Via Light Scattering

| Formulation # | R | Molecular Weight (Daltons, ×10$^5$) | $R_G$ (nm) | $R_H$ (nm) |
|---|---|---|---|---|
| CPAA 1 | 0.25 | 35.4 | 47.4 | 97.6 |
| CPAA 2 | 0.50 | 21.1 | 45.8 | 88.8 |
| CPAA 3 | 0.75 | 17.6 | 42.3 | 88.2 |
| CPAA 4 | 1.00 | 17.9 | 40.40 | 90.7 |
| CPAA 5 | 1.26 | 10.3 | 67.50 | 60.55 |
| CPAA 6 | 1.49 | 9.38 | 63.00 | 56 |
| CPAA 7 | 1.76 | 9.33 | 63.50 | 57.65 |
| CPAA 8 | 2.01 | 7.35 | 56.10 | 49.55 |
| CPAA 9 | 3.00 | 5.72 | 60.90 | 42.25 |
| CPAA 10 | 4.04 | 4.66 | 64.60 | 38.15 |

Measurements indicate that stable associative PECs with $R_G$ less than or equal to 300 nm (corresponding to diameters less than about 600 nm) can be produced via the inventive processes described herein, over a range of R values.

Example 13

Chitosan/PAA PECs Containing Antimicrobial Metal Ions

Many metal and transition metal cations, such as silver ions, are well known to the art to exhibit anti-microbial activity. In one embodiment employing the associative PECs of the present invention, associative PECs may be used to anchor silver ions onto surfaces, through treatment of the surface with associative PECs containing silver ions, or alternatively employing a two-step treatment process similar to that described in Examples 10 and 11. The ability of associative PECs to modify surfaces, as described hereinabove, can be thus be used to easily provide a wide variety of treated surfaces exhibiting residual antimicrobial activity afforded via silver (or other germicidal metal ions), in product executions in which quaternary ammonium biocides are not preferred, for aesthetic or safety reasons, or in the case of products perceived as more "natural" or "sustainable" by consumers, in which a biocide which is produced from non-petrochemical materials is desired.

Exemplary associative PECs decorated with silver ions ($Ag^+$) are assembled using the initial steps of the process described for the production of the formulations summarized in Table 1B.

TABLE 13.1

Compositions of Chitosan/PAA PECs with Silver Ions

| Formulation # (a) | R | Chitosan Stock A (mL) | Alcosperse 465 Stock B (mL) | 10 wt % Citric Acid (mL) | Tinosan SDC (mL) (b) | $H_2O$ (mL) | Total concentration charged groups (mM) | Total Ag+ Ion (ppm) |
|---|---|---|---|---|---|---|---|---|
| CPAG 1 | 0.25 | 8.21 (1) | 9.42 (2) | 12.03 | 4.1 | 267.21 | 1.29 | 29.9 |
| CPAG 2 | 0.50 | 13.79 (1) | 7.91 (2) | 9.56 | 4.1 | 265.58 | 1.30 | 30.1 |
| CPAG 3 | 0.75 | 17.71 (1) | 6.76 (2) | 7.79 | 4.1 | 264.54 | 1.30 | 30.1 |
| CPAG 4 | 1.00 | 20.65 (1) | 5.95 (2) | 6.53 | 4.1 | 263.69 | 1.31 | 30.1 |
| CPAG 5 | 1.25 | 23.01 (2) | 5.27 (1) | 5.46 | 4.1 | 263.05 | 1.30 | 30.0 |
| CPAG 6 | 1.50 | 24.72 (2) | 4.74 (1) | 4.71 | 4.1 | 262.62 | 1.30 | 30.2 |
| CPAG 7 | 1.75 | 26.22 (2) | 4.31 (1) | 4.07 | 4.1 | 262.18 | 1.30 | 30.2 |
| CPAG 8 | 2.01 | 27.48 (2) | 3.93 (1) | 3.48 | 4.1 | 261.83 | 1.30 | 30.3 |
| CPAG 9 | 2.99 | 31.02 (2) | 2.98 (1) | 1.88 | 4.1 | 260.83 | 1.31 | 29.9 |
| CPAG 10 | 4.00 | 32.90 (2) | 2.36 (1) | 1.04 | 4.1 | 260.36 | 1.30 | 30.0 |

(X) Denotes order of addition, "1" being the minor component and "2" the major component.
(a) Materials and stock solutions as described in Table 1A.
(b) Source of $Ag^+$ ions, obtained from Pure Biosciences, Inc.

The molecular weights and particle sizes of the associative PECs in the solutions in Table 13.1 were determined as described above, resulting data summarized in Table 13.2.

TABLE 13.2

Molecular Weights and Radii of Stable Chitosan/PAA PECs Decorated with $Ag^+$ ions, Determined Via Light Scattering

| Formulation # | R | Molecular Weight (Daltons, ×10$^6$) | $R_G$ (nm) | $R_H$ (nm) |
|---|---|---|---|---|
| CPAG 1 | 0.25 | 26.3 | 122.8 | 173.3 |
| CPAG 2 | 0.5 | 20.8 | 134.8 | 221.3 |
| CPAG 3 | 0.75 | 11.1 | 117.1 | 205.6 |
| CPAG 4 | 1 | 8.46 | 133.9 | 187.4 |
| CPAG 5 | 1.25 | 4.59 | 98.5 | 159.5 |
| CPAG 6 | 1.5 | 4.88 | 114.1 | 188.4 |
| CPAG 7 | 1.75 | 6.76 | 111.7 | 249.4 |
| CPAG 8 | 2 | 6.61 | 111.8 | 282.2 |
| CPAG 9 | 3 | 5.39 | 144.9 | 193 |
| CPAG 10 | 4 | 4.84 | 145.8 | 214.5 |

Results in Table 13.2 indicate that stable associative PECs with $R_G$ and or $R_H$ less than 300 nm (corresponding to diameters less than about 600 nm) can be produced via the methods described herein, over a wide range of R values. The data also indicate that the molecular weights of the associative PECs in solutions containing soluble $Ag^+$ ions are significantly larger than in the case of associative PECs of similar composition made in the absence of $Ag^+$ ions, indicating significant uptake and/or association of the silver ions with the associative PECs without inducing displacement of the cationic chitosan component or phase separation or precipitation in the inventive treatments, which all remained clear and stable, and produced thin invisible films on treated glass surfaces.

Example 14

Concentration Ranges for Production of Stable Chitosan/PAA PECs Formed Near R=1.0

This example illustrates associative PECs prepared using a different chitosan source were the amount of PAA (poly (acrylic acid)) was fixed but with varying molecular weights of PAA compared. Surprisingly, stable Chitosan/PAA PECs with compositions corresponding to values of R=1.0 can be made according to the methods of the present invention by selecting the appropriate order of addition of the polymers and using concentrations of the polymer stock solutions that are not excessively high, for example, in one embodiment where the total combined concentration of charged groups on the associative PECs polymers are below about 25 mM.

TABLE 14.1

| R (1) | Chitosan Stock (mL) (2) | PAA Stock (mL) (3) | 10 wt % Citric Acid (mL) (4) | H$_2$O (mL) | Total final volume (mL) | Total concentration charged groups (mM) | Stable and Clear Solution Obtained? |
|---|---|---|---|---|---|---|---|
| 1.05 | 0.4398 | 0.1459 | 1.2114 | 16.7363 | 18.5334 | 0.53 | yes |
| 1.06 | 2.0749 | 0.6811 | 0.5491 | 15.3039 | 18.6090 | 2.49 | yes |
| 1.04 | 5.0044 | 1.674 | — | 11.8330 | 18.5114 | 6.10 | yes |
| 1.03 | 8.0199 | 2.7068 | — | 7.8212 | 18.5479 | 9.81 | yes |
| 1.04 | 12.0289 | 4.0102 | — | 2.5027 | 18.5418 | 14.63 | yes |
| 1.03 | 14.0127 | 4.7177 | — | — | 18.7304 | 16.95 | yes |

(1) All compositions 16.95 mM final concentration in terms of the total charged groups present.
(2) 0.2 wt % Univar chitosan, Pharma grade, lot WA200701010), average MW or 1.0 × 10$^5$ Daltons
(3) 0.235 wt % Alcosperse 465 (Alco Chemical), average MW 8.0 × 10$^3$ Daltons.
(4) 0.7 wt % final citrate level in all compositions.

Associative PECs formulations described in Table 14.2 were made in the same manner as described for those in Table 14.1 and indicate that stable associative PECs may be assembled using the methods of the present invention to yielding Chitosan/PAA PECs with R values very close to 1.

TABLE 14.2

| R (1) | Chitosan Stock (mL) | PAA Stock (mL) | 10 wt % Citric Acid (mL) | H$_2$O (mL) | Total final volume (mL) | Total concentration charged groups (mM) | Stable and Clear Solution Obtained? |
|---|---|---|---|---|---|---|---|
| 1.06 | 0.4522 | 0.3724 | 1.1962 | 16.5387 | 18.5595 | 1.37 | yes |
| 1.05 | 2.0206 | 1.6786 | 0.5364 | 14.2945 | 18.5301 | 6.14 | yes |
| 1.03 | 5.0152 | 4.227 | — | 9.3048 | 18.5470 | 15.34 | yes |

(1) All compositions 15.34 mM final concentration in terms of the total charged groups present.

Example 15

The following embodiments of the present invention explore concentration ranges for production of stable Chitosan/PAA PECs using an alternative PAA source for values of R approaching 1.0.

TABLE 15.1

| R | Chitosan Stock (mL) (1) | PAA Stock (mL) (2) | 10 wt % Citric Acid (mL) | H$_2$O (mL) | Total final volume (mL) | Total concentration charged groups (mM) | Stable and Clear Solution Obtained? |
|---|---|---|---|---|---|---|---|
| 1.06 | 0.4522 | 0.3724 | 1.1962 | 16.5387 | 18.5595 | 1.37 | yes |
| 1.05 | 2.0206 | 1.6786 | 0.5364 | 14.2945 | 18.5301 | 6.14 | yes |
| 1.03 | 5.0152 | 4.227 | 0.0000 | 9.3048 | 18.5470 | 15.34 | yes |
| 1.04 | 8.0262 | 6.7122 | 0.0000 | 3.8109 | 18.5493 | 24.45 | yes |
| 1.04 | 10.0828 | 8.4495 | 0.0000 | 0.0000 | 18.5323 | 30.78 | yes |

(1) 0.5 wt % Univar chitosan
(2) 0.235 wt % Aquatreat AR-7H (Alco Chemical). average MW 8.7 × 10$^5$ Daltons The Chitosan/PAA PECs were assembled using the same procedure as in Example 13. Results in Table 15.1 indicate that stable associative PECs may be assembled with the process and stocks described, yielding a solution of Chitosan/PAA PECs that had a final concentration, in terms of the total charged groups present of at least 30.78 mM.

Example 16

PECs Comprising Two Natural Polymers

Associative PECs containing two natural polymers, such as chitosan derived from crustacean shells, and alginic acid, may be used for the formation of natural polymer derived associative PECs. Further, use of natural or naturally-derived, surfactants produced from sustainable, non-petrochemical feedstocks enable completely natural associative PECs compositions to be made. Reducing the environmental impact of household products through the use of materials produced in a natural and/or more sustainable manner is of great interest to a significant number of consumers today.

TABLE 16

Compositions of Chitosan/Alginate PECs with and without Nonionic Surfactant

| Formulation # | R | Chitosan Stock A (g) (a) | Sodium Alginate, Stock B (g) (b) | $H_2O$ (g) | Glucopon Stock (g) (c) | Total concentration charged groups (mM) |
|---|---|---|---|---|---|---|
| CAL 1 | 0.10 | 0.23 (1) | 2.4 (2) | 16.38 | 1.0 | 1.50 |
| CAL 2 | 5.0 | 2.05 (2) | 0.44 (1) | 17.51 | — | 1.52 |
| CAL 3 | 5.0 | 2.05 (2) | 0.44 (1) | 16.52 | 1.0 | 1.52 |
| CAL 4 | 10.0 | 2.2 (2) | 0.24 (1) | 17.56 | — | 1.50 |
| CAL 5 | 10.0 | 2.2 (2) | 0.24 (1) | 16.57 | 1.0 | 1.50 |

(a) Stock A: 0.2 wt % chitosan (Federal Labs) and 0.7 wt % citric acid in deionized water
(b) 0.2 wt % sodium alginate from Sigma-Aldrich, # W201502 (from brown algae).
(c) 1 wt % Glucopon 325N surfactant in deionized water. 1 min stirring.
(1, 2) Order of addition: Polymer solution added (1) to deionized water or (2) to first polymer solution.

The modification of the Ge surface of an IRE using the inventive associative PEC formulations of Table 16 was investigated to illustrate that all natural Chitosan/Alginate PECs can be utilized in products such as surface treatments or hard surface cleaners, which may or may not be allowed to dry on the treated surface.

TABLE 16.1

Characterization of Layers Formed With Chitosan/Alginate PECs

| Formulation # | Acid C=O Band Alginic acid (mAU) | Alginate Carboxylate groups (mAU) | Chitosan and Alginate C—O Band (mAU) | "C" Water uptake in PEC layer (mAU) | Treatment (1) Number of Water Rinses |
|---|---|---|---|---|---|
| CAL 1 | 1.55 | 1.40 | 3.86 | 3.496 | Dried, 50 |
| CAL 1 | 1.39 | 1.31 | 3.67 | 3.316 | 100 |
| CAL 2 | 0.24 | 0.545 | 1.885 | 0.788 | 50 |
| CAL 3 | 0.158 | 0.454 | 1.934 | 1.149 | 50 |
| CAL 4 | 0.192 | 0.364 | 1.920 | 1.378 | 50 |
| CAL 4 | 0.192 | 0.403 | 1.980 | 1.458 | 50 (2) |
| CAL 5 | 0.188 | 0.375 | 1.790 | 0.86 | 50 |
| CAL 5 | 0.205 | 0.475 | 1.882 | 1.087 | 50 (2) |

(1) 5 minute absorption time without drying unless otherwise noted, followed by number of rinses indicated.
(2) CAL 4 and 5 formulations reapplied in a second application followed by addition rinses indicated Results in Table 16.1 indicate that formulations both with and without surfactant (here a naturally derived alkyl polysaccharide) are able to deliver significant hydrophilic modification to a treated surface even with relatively high surfactant concentration present. Results further indicate that these exemplary formulations deliver relatively rapid modification of the surface in a "self-limiting" manner despite repeated applications, as was discussed in other examples above.

Dynamic Light Scattering Characterization of Chitosan/Alginate PECs

Dynamic light scattering (DLS) was used to measure the particle sizes of some Chitosan/Alginate PEC formulations. Those skilled in the art will realize that it is sometimes possible via dynamic light scattering to detect the presence of more than one population of particles in a mixture, especially when the average sizes of the populations are large, and the polydispersity of sizes of the populations is relatively small. The data in Table 16.2 indicate that the largest scattering particles present in the Chitosan/Alginate PECs formulations all exhibit average hydrodynamic radii ($R_h$) less than 300 nm, consistent with the stability and clear appearance of the formulations. In the cases where average radii could be calculated for two populations, it is believed, without being bound by theory, that peaks with the smallest $R_h$ values could be due to soluble polymeric species incorporated into the solutions that originate from the natural polymer raw materials.

TABLE 16.2

Dynamic Light Scattering of Chitosan/Alginate PECs

| Formulation # | R | Peak 1 $R_h$ (nanometers) | Peak 2 $R_h$ (nanometers) |
|---|---|---|---|
| CAL 1 | 0.1 | 10 | 93 |
| CAL 2 | 5.0 | 27 | 169 |
| CAL 3 | 5.0 | 103 | Not detected |
| CAL 4 | 10.0 | 20 | 128 |
| CAL 5 | 10.0 | 18 | 132 |

Example 17

Atomic Force Microscopy Images of Layers Formed by PECs

Images of the layers formed by exposure of surfaces to stable associative PECs can be obtained via atomic force microscopy (AFM). The images shown were obtained in Non-Contact "Tapping" Mode using a Veeco CP-II Atomic Force Microscope (AFM). AFM tips were Veeco RTESPA-CP mounted tips (1-10 Ohm-cm Phosphorus (n) doped Si) with a resonant frequency approximately between 256-295 kHz, and a spring constant approximately between 20-80

N/m. The resonant frequency for each tip was determined experimentally and applied prior to image acquisition. Software used for image acquisition was a Veeco Digital Instruments model CP-11 Proscan 1.8.

FisherFinest Premium Microscope Slides were exposed to the associative PECs formulations for five minutes, followed by rinsing with 250 mL of high quality water provided by a Barnstead NanoPure system. Treated and rinsed slides were then dried in air protected from dust prior to AFM imaging.

Multiple images were collected per surface-treatment to substrate combination. For each image, Topography and Phase data were acquired in both scan directions and compared for similarity. For example, each image in a horizontally acquired scan would have forward and reverse topography and phase data. Scan rate was set between 0.25-1 Hz. Scan sizes ranged from 0.25 to 5 square microns. Set points were between −0.04 and −0.06 microns. Topography images acquired with Proscan 1.8 were processed using Image Processing and Data Analysis, version 2.1.15, by TM Microscopes. Additional details on the practice of AFM can be found in "Noncontact Atomic Force Microscopy", S. Morita, R. Wiesendanger, E. Meyer, Eds. Springer-Verlag: Berlin, Heidelberg, New York. $1^{st}$ Ed, 2002, incorporated herein by reference.

Figure 3:
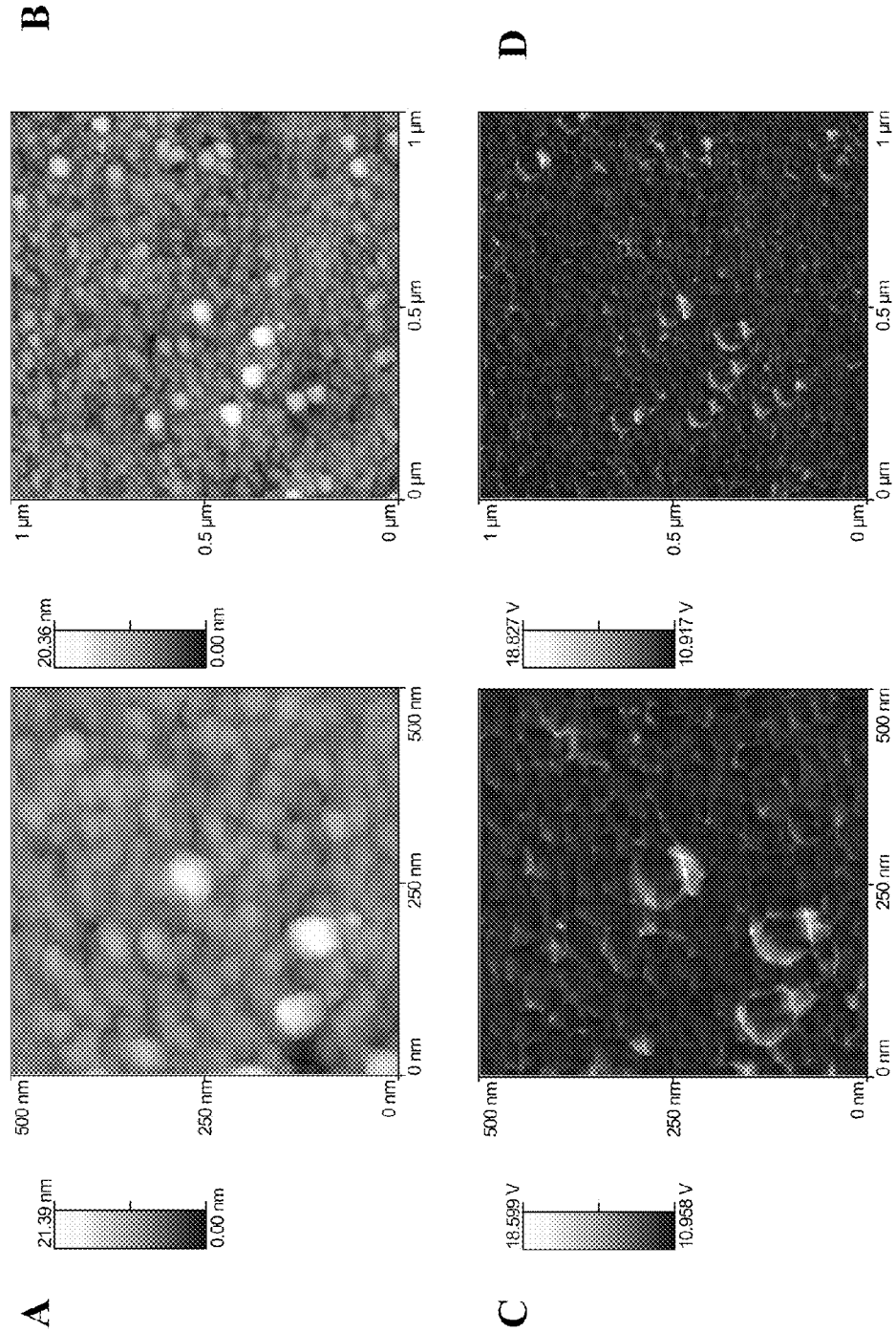
FIG. 3 shows atomic force microscopic images of Chitosan/PAA PECs (R=0.25) on a glass surface treated with formulation CPAA1. Top row (A and B) views are topographic images, while the bottom row (C and D) are phase images. Dimension of area images (A, C) is 500 by 500 nanometers, and 1.0 by 1.0 micrometers for images (B, D).
Figure 4:
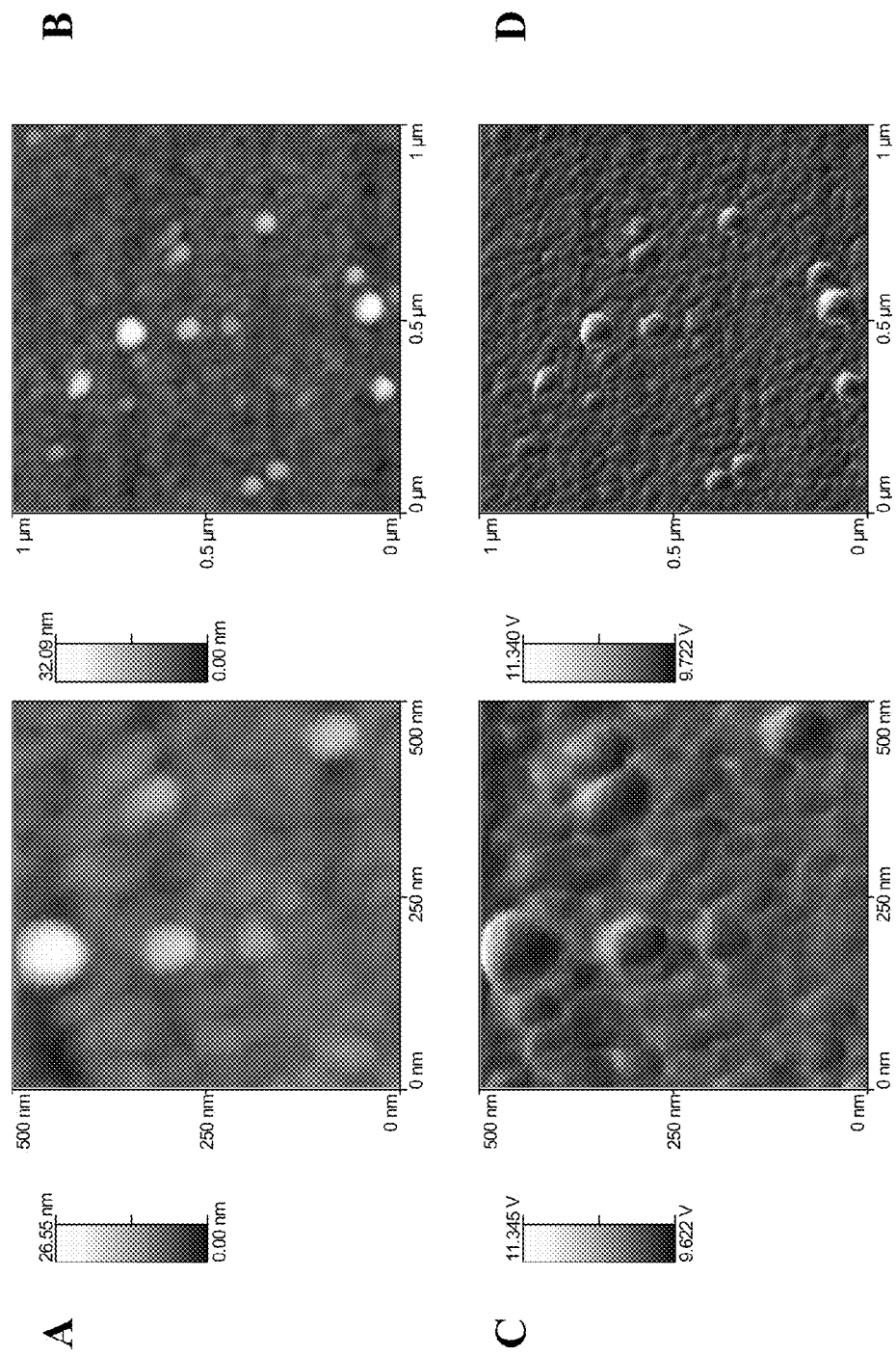
FIG. 4 shows atomic force microscopic images of Chitosan/PAA PECs (R=0.25) on a glass surface treated with formulation CPAAG1. Top row (A and B) views are topographic images, while the bottom row (C and D) are phase images. Dimensions same as FIG. 3.

The AFM images of a layer formed on glass slides from exposure to a Chitosan/PAA PEC formulation without added silver ions, with a R parameter of 0.25 (formulation CPAA 1, Table 1B) and a layer formed on glass slides from exposure to a Chitosan/PAA PEC formulation (R=0.25) which contained silver ions (formulation CPAG 1, Table 13.1) were obtained, the images shown in FIGS. 3 and 4. Table 17.1 summarizes the characterization of the images of the layers on glass formed from exposure to these associative PECs formulations.

TABLE 17.1

Topographical Characteristics of AFM Images of PECs Layers on Glass

| Topographical Parameter | Formulation | |
| --- | --- | --- |
| | CPAA 1 (1) | CPAG 1 (2) |
| Diameter of PEC particle (nm) | 50-100 | 100-150 |
| Height of PEC particle (nm) | 10-15 | 25 |
| (min and max range in nm) | (7-17) | (20-40) |
| Number of particles analyzed | 373 | 285 |

(1) See FIG. 3 image on glass substrate
(2) See FIG. 4 image on glass substrate

Results shown in FIGS. 3 and 4, and Table 17.1 indicate that the glass surface exposed to the formulations followed by rinsing (i.e., no drying step of the formulation onto the glass) acquire a significant number of associative PEC particles. The particles appear to be roughly circular and of uniform dimension, having thicknesses significantly less than their diameters. Thus, the topography data suggest that the particles are "pancake-like" in shape. The data also show that the associative PECs having silver ions present appear a bit larger. The "phase" images also can be interpreted to mean that the mechanical properties (stiffness, resistance to flow) of the particles in the images are all very similar, and are thus of very similar if not identical chemical composition.

Example 18

Scanning Electron Microscopy

Electron Images of Layers of PECs with Silver Ions

Figure 5A:
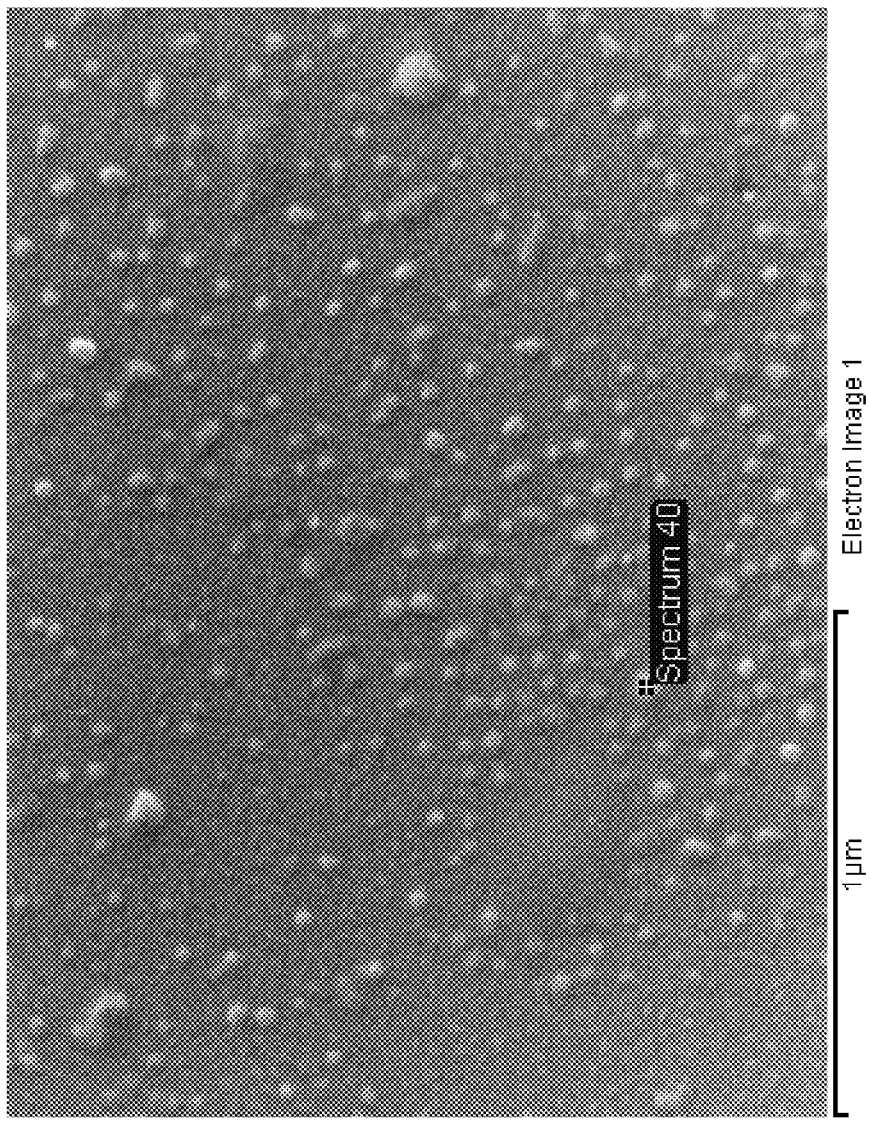
FIG. 5A shows a secondary electron image of a layer formed on glass through exposure to formulation CPAG1. The corresponding
Figure 5B:
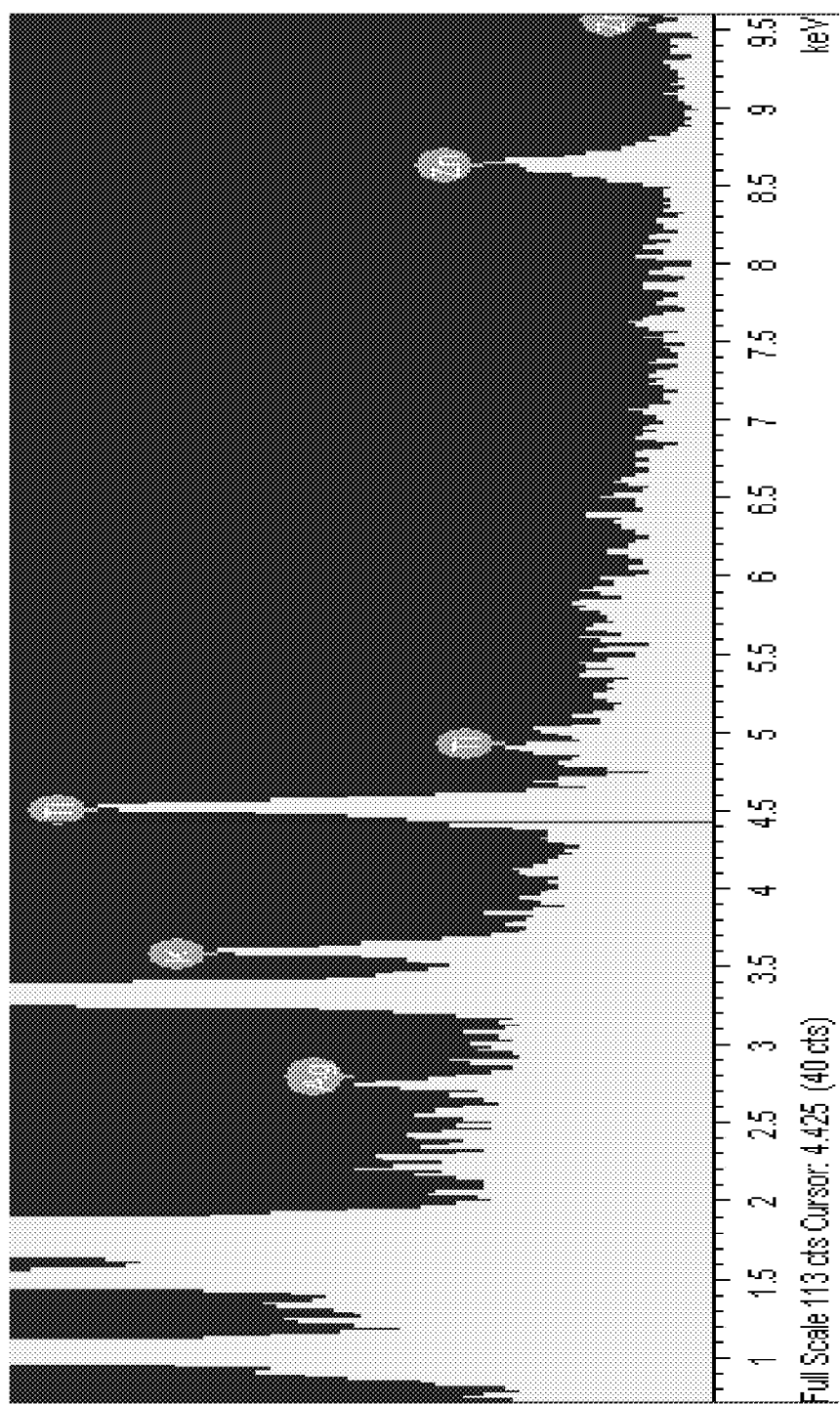
FIG. 5B shows the elemental composition with characteristic X-ray emission spectrum in KeV of species present at the "+" spot sampled indicated and labeled as "Spectrum 40".
Figure 6A:
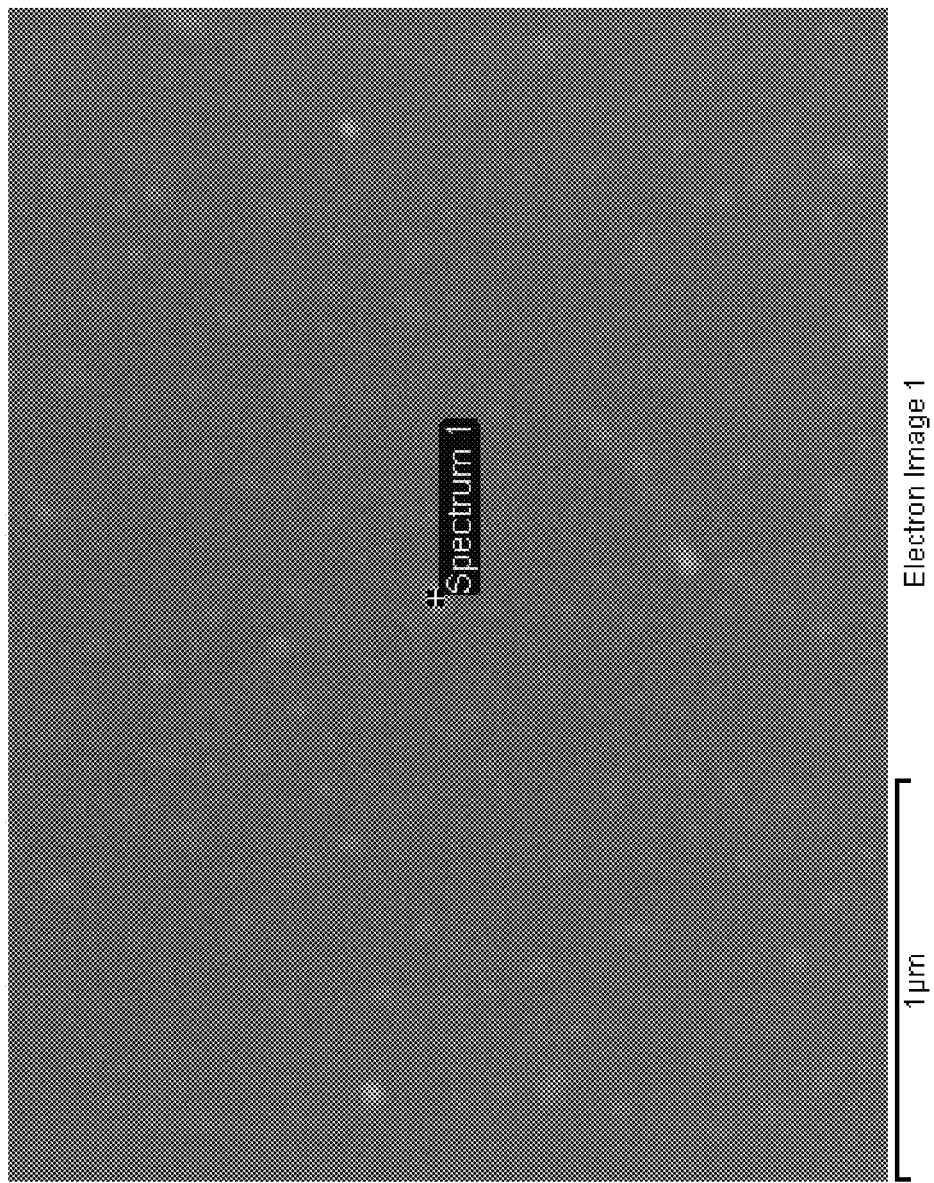
FIG. 6A shows another electron image of an associative PEC particle in the same layer prepared in Example 18. The corresponding
Figure 6B:
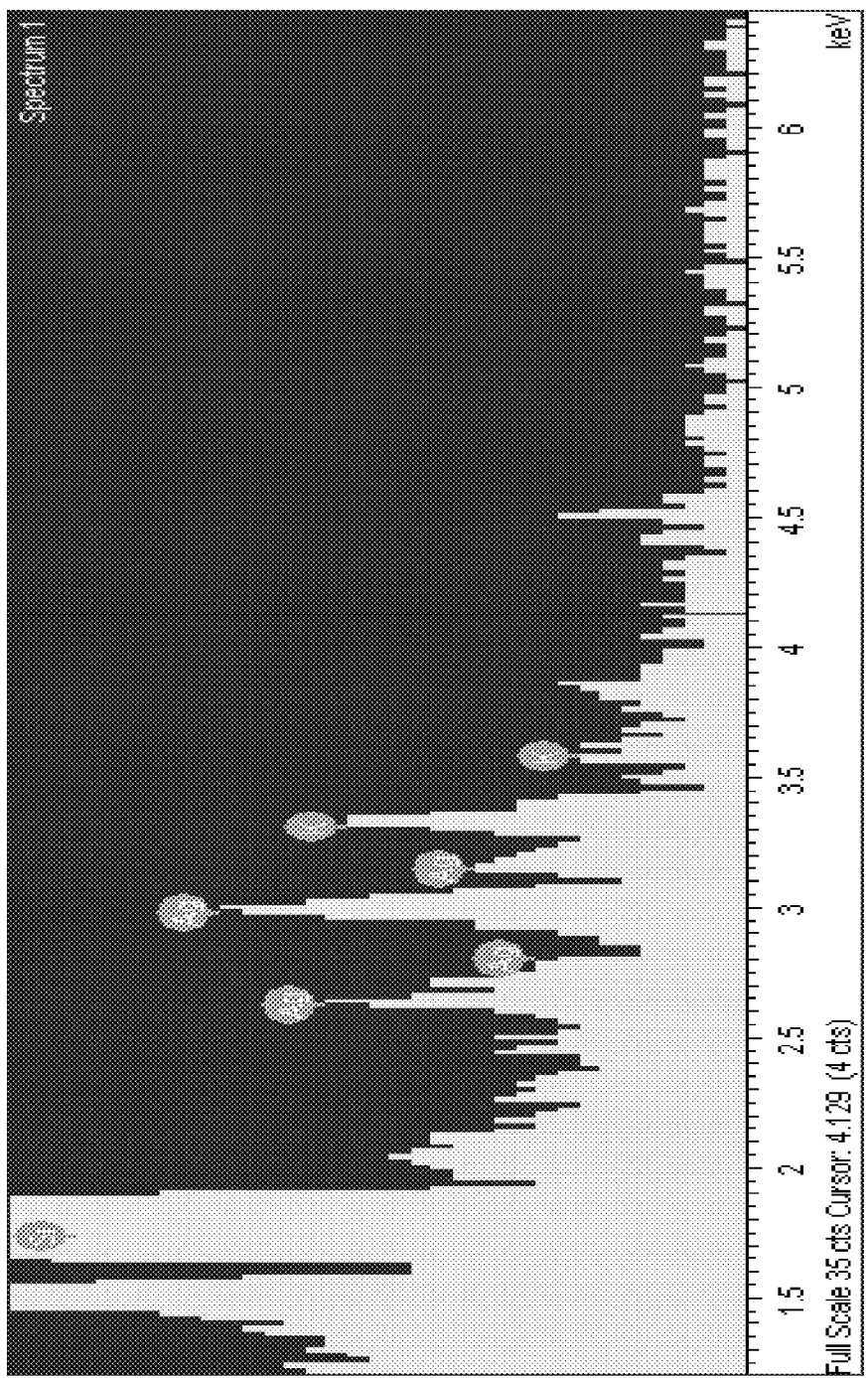
FIG. 6B shows the elemental composition with characteristic X-ray emission spectrum in KeV of species present at the "+" spot sampled indicated and labeled as "Spectrum 1".

FIG. 5A shows a secondary electron image of a layer formed on glass through exposure to formulation CPAG1. The layer was prepared in the same manner as that described in AFM image study, Example 17. A particular associative PEC particle was selected for elemental analysis, as indicated by the cursor location in the electron image labeled "spectrum 40". The X-ray spectrum of this particular particle is also shown in FIG. 5B. Results support the presence of silver ions in the invisible layers formed on glass from exposure to Chitosan/PAA PEC treatment compositions.

Example 19

PECs Formulation with Anionic Surfactant and Buffer System

The stability of the associative PECs taught herein is not believed to be a function of the pH of the formulations, provided that the polymers comprising the associative PECs are soluble in the stock solutions used and the appropriate order of addition, with respect for a given desired R value, is employed. It is possible to create stable associative PECs in formulations that contain significant amounts of buffering salts, which may be required for the chemical stability of other formulation ingredients. As an example embodiment of a salt tolerant associative PECs formulation, DADMAC/PAA PECs were assembled in a concentrated borate buffer. The anionic surfactant, being charged, was added after assembly of the associative PECs as shown in Table 18.1, resulting in stable associative PECs formulations at pH 8 with high buffer levels and surfactant present.

TABLE 18.1

| Formulation # | R | SAS Concentration (wt %) (1) | Anionic charge from PAA (mM) (2) | Cationic charge from DADMAC (mM) (3) | Total concentration charged groups (mM) |
| --- | --- | --- | --- | --- | --- |
| IB-6 | 0.25 | 0.132 | 1.22 | 0.298 | 1.52 |

(1) 3 wt % secondary alkane sulphonate surfactant (Hostapur SAS 30, from Clariant Corp.), pH 8 borate buffer.
(2) Polymer stock solution of PAA (Aquatreat AR-4) 10 mM concentration of anionic acid groups, 0.073 wt %.
(3) PDADMAC (Floquat FL 4540, SNF Corp., 10 mM concentration of cationic groups, 0.161 wt %)

Commercial Examples

Table 19 illustrates embodiments of the present invention employing commercially available ingredients to form associative. PECs treatment compositions having utility in cleaning and disinfection of common household and commercial surfaces, all providing hydrophilic modification of the treated surfaces in addition to other benefits enabled by the optional adjuncts present.

TABLE 19

| Ingredient | A | B | C | D | E | F | G | H | I |
|---|---|---|---|---|---|---|---|---|---|
| Glucopon ®325N (APG) | 0.1 | 0.04 | | | | | | | |
| Barquat 4250Z ® | 0.06 | 0.3 | | | | | | | |
| Chitosan (Federal Labs) | 0.0047 | 0.019 | | | 0.02 | | | | |
| Alcosperse 465 ® (PAA) | 0.0075 | 0.002 | 0.00735 | | | | | | |
| Citric acid | 0.75 | 0.75 | 0.40 | 1.25 | 0.075 | | | | |
| Chitosan (Sigma-Aldrich) | | | 0.0055 | | | | | | |
| Glucopon 425N ® (APG) | | | 0.75 | 3.00 | | | | | |
| Tinosan SDC (silver dihydrogen citrate) | | | 0.0136 | | | | | | |
| Chitosan (Univar) | | | | 0.135 | | | | | |
| Aquatreat AR-7H ® (PAA) | | | | 0.053 | | | | | |
| Sodium alginate | | | | | 0.0025 | | | | |
| Radia ® Easysurf 6781 (alkyl polypentoside) | | | | | 3.0 | | | | |
| Aquatreat AR-4 ® (PAA) | | | | | | 0.0087 | 0.0071 | 0.0033 | 0.0039 |
| Floquat 4540 ® (PolyDADMAC) | | | | | | 0.0048 | 0.0081 | 0.0072 | 0.0073 |
| Hostapur SAS30 | | | | | | 0.15 | | | |
| Boric acid | | | | | | 0.6 | | | |
| Potassium carbonate | | | | | | | | 1.64 | |
| Sodium hydroxide | | | | | | To pH 8.0 | To pH 11.2 | To pH 11.2 | 0.1 |
| Sodium silicate | | | | | | | 0.016 | | |
| Ammonyx LO ® | | | | | | | | 0.04 | 1.0 |
| Sodium hypochlorite | | | | | | | 0.025 | 2.0 | |
| Fragrance | 0.02 | 0.10 | 0.15 | 0.10 | 0.10 | 0.02 | | 0.1 | 0.1 |
| Deionized water | balance | balance | balance | balance | balance | balance | balance | balance | balance |

Key:
A = Disinfecting cleaner
B = Disinfecting lotion for use on nonwoven substrate containing wood pulp
C = Disinfecting cleaner with silver ion antimicrobial
D = Toilet Bowl Cleaner
E = Natural Hard Surface Cleaner
F = Mild pH Daily Shower Cleaner
G = Daily Shower Cleaner with Bleach
H = Mildew Remover with Bleach
I = Toilet Bowl Cleaner In other embodiments, formulations containing associative PECs and hypochlorous acid (HOCl) derived from solutions of sodium hypochlorite through adjustment of the pH of the aqueous carrier can be produced. Such embodiments are useful for the reduction of germs and the removal of stains from a wide variety of surfaces. The presence of the PECs in such formulations, besides providing hydrophilic surface modification benefits as described above, also improves the surface wetting and cleaning properties of solutions of HOCl, which is known to be a powerful oxidant.

In one embodiment of the invention, compositions comprising PECs and hypochlorous acid derived from solutions of sodium hypochlorite through the adjustment of pH also comprise a buffer. Suitable buffers include but are not limited to: organic acids, mineral acids, alkali metal and alkaline earth salts of silicate, metasilicate, polysilicate, borate, carbonate, carbamate, phosphate, polyphosphate, pyrophosphates, triphosphates, tetraphosphates, ammonia, hydroxide, monoethanolamine, monopropanolamine, diethanolamine, dipropanolamine, triethanolamine, and 2-amino-2methylpropanol. In one embodiment, preferred buffering agents for compositions of this invention include but are not limited to, dicarboxlic acids, such as, succinic acid and glutaric acid.

Table 20 lists some compositions containing PECs comprising PAA and poly(DADMAC) at various R values, HOCl and succinic acid as a buffer. The phase stability was assessed visually, and the HOCl stability was determined via titration of the samples stored at high temperature in an acceleration of the aging of the systems.

TABLE 20

Formulas containing HOCl with R = 0.5-2.0

| Sample # | R | PAA mM | PDADMAC mM (3) | HOCl mM | Succinate mM | Phase Stable (4) | % HOCl remaining |
|---|---|---|---|---|---|---|---|
| 1.1 | 0.50 | 1.00 | 0.5 | 1.34 | 1.01 | Yes | 5% |
| 1.2 | 0.62 | 0.89 | 0.55 | 1.34 | 1.01 | Yes | 22% |
| 1.3 | 0.79 | 0.84 | 0.66 | 1.34 | 1.01 | Yes | 31% |
| 1.4 | 0.89 | 0.79 | 0.71 | 1.34 | 1.01 | Yes | 40% |
| 1.5 | 1.11 | 0.71 | 0.79 | 1.34 | 1.01 | Yes | 51% |
| 1.6 | 1.24 | 0.67 | 0.83 | 1.34 | 1.01 | Yes | 58% |
| 1.7 | 1.42 | 0.62 | 0.88 | 1.34 | 1.01 | Yes | 60% |
| 1.8 | 1.65 | 0.57 | 0.94 | 1.34 | 1.01 | Yes | 68% |
| 1.9 | 1.99 | 0.50 | 1.00 | 1.34 | 1.01 | Yes | 61% |
| 1.10 | N/A | 0.00 | 0.00 | 1.34 | 1.01 | Yes | 95% |

(1) Total volume of samples 150 mL, pH 5.75
(2) Alco Aquatreat AR-4
(3) SNF Floquat 4540
(4) Stored at 49° C. for 2 days
*N/A stands for not applicable. (Shown in Tables where R values cannot be calculated)

The results in Table 20 show that at pH 5.75, PECs that are phase stable can be produced with PAA and poly(DADMAC) over a range of R values. The control sample 1.10 exhibits good stability of HOCl under accelerated aging conditions, and in Table 20 the PECs formulations in which R is greater than about 0.5 are preferred. The PECs formulations in Table 20 with R values greater than about 1.0 show improved HOCl stability. Surprisingly, the stability of the HOCl increases as the R value (and hence the amount of poly(DADMAC) in the formulation) of the PECs increases.

Table 21 lists a series of formulations containing PECs comprising PAA and poly(DADMAC) at low pH, about 5.75, but in the absence of HOCl and succinic acid buffer.

TABLE 21

Formulas without buffer and without HOCl with R = 0.5-2.0

| Sample # (1) | R | PAA mM (2) | PDADMAC mM (3) | HOCl mM | Succinate mM | Phase Stable (4) |
|---|---|---|---|---|---|---|
| 2.1 | 0.50 | 1.00 | 0.50 | 0.0 | 0.0 | Yes |
| 2.2 | 0.60 | 0.94 | 0.56 | 0.0 | 0.0 | Yes |
| 2.3 | 0.60 | 0.89 | 0.62 | 0.0 | 0.0 | No |
| 2.4 | 0.80 | 0.83 | 0.67 | 0.0 | 0.0 | No |
| 2.5 | 0.90 | 0.79 | 0.71 | 0.0 | 0.0 | No |
| 2.6 | 1.11 | 0.71 | 0.79 | 0.0 | 0.0 | Yes |
| 2.7 | 1.25 | 0.67 | 0.83 | 0.0 | 0.0 | Yes |
| 2.8 | 1.43 | 0.62 | 0.88 | 0.0 | 0.0 | Yes |
| 2.9 | 1.67 | 0.56 | 0.94 | 0.0 | 0.0 | Yes |
| 2.10 | 1.99 | 0.50 | 1.00 | 0.0 | 0.0 | Yes |
| 2.11 | N/A | 0.00 | 0.00 | 0.0 | 0.0 | Yes |

(1) Total volume of samples 150 mL, pH 5.75 adjusted with HCl
(2) Alco Aquatreat AR-4
(3) SNF Floquat 4540
(4) Stored at 22° C. for 3 days The data in Table 21 show that PECs comprising PAA and poly(DADMAC) can be produced at low pH, about 5.75, over a wide range of R values. However, the formulations with R values between about 0.6 and 0.9 were not phase stable at the total polymer concentration of about 1.5 mM, which is similar to the compositions reviewed in Table 20, in the absence of HOCl and succinic acid buffer. The inventors believe, without being limited by theory, that HOCl and/or the succinic acid buffer can partially "screen" the anionic charges of the PAA carboxylate groups from the cationic groups of the poly(DADMAC) and thus can enable formulation of PECs with R values nearer 1.0 than in the absence of the buffer or HOCl. Thus, the R value of the PECs may be adjusted to provide stable formulations even in the presence of a buffer suitable for use with HOCl as an oxidant.

Table 22 describes some formulations comprising PECs and HOCl as an oxidant in which the pH is about neutral, i.e., pH 7.0.

TABLE 22

Formulas comparing PECs to single polymer solution

| Sample # | R | PAA mM (2) | PDADMAC mM (3) | HOCl mM | Succinate mM | Phase Stable (4) | % HOCl remaining (4) |
|---|---|---|---|---|---|---|---|
| 3.1 | 0.49 | 1.01 | 0.5 | 1.37 | 1.02 | Yes | 12% |
| 3.2 | 3.9 | 0.30 | 1.20 | 1.37 | 1.02 | Yes | 56% |
| 3.3 | N/A | 1.52 | 0.0 | 1.37 | 1.01 | Yes | 85% |
| 3.4 | N/A | 0.0 | 1.50 | 1.37 | 1.02 | Yes | 23% |
| 3.5 | N/A | 0.0 | 0.0 | 1.37 | 1.02 | Yes | 92% |

(1) Total volume of samples 150 mL, pH 7.0
(2) Alco Aquatreat AR-4
(3) SNF Floquat 4540
(4) Stored at 49° C. for 4 days The results in Table 22 show that phase stable PECs comprising PAA and poly(DADMAC) can be produced in solutions also comprising HOCl as a buffer when the pH is adjusted to about 7.0, at R values both below and above 1.0. The control sample 3.5 shows good stability of the HOCl under accelerated testing conditions. Sample 3.3 contains HOCl and only the single polymer poly(acrylic acid), and exhibits very good stability. Sample 3.4 contains HOCl and only the single polymer poly(DADMAC), and this sample exhibits significantly more, loss of HOCl than in samples 3.3 or 3.5. Surprisingly, in the presence of PECs made with both polymers, at a R value greater than 1.0 (sample 3.2) the HOCl stability is significantly better than in the case of the addition of poly(DADMAC) alone, or even in the case of sample 3.1, at a R value less than 1.0, in which the PAA is present in the PECs in excess.

Table 23 describes some compositions comprising PECs and HOCl as an oxidant in which the pH is adjusted to about neutral, pH 7.0

TABLE 23

Formulas containing HOCl with R = 0.5-8.0

| Sample # (1) | R | PAA mM (2) | PDADMAC mM (3) | HOCl mM | Succinate mM | Phase Stable (4) | % HOCl remaining (4) |
|---|---|---|---|---|---|---|---|
| 4.1 | 0.50 | 1.00 | 0.5 | 1.37 | 1.01 | Yes | 33% |
| 4.2 | 2.0 | 0.50 | 1.00 | 1.37 | 1.01 | Yes | 58% |
| 4.3 | 3.9 | 0.30 | 1.20 | 1.37 | 1.01 | Yes | 72% |
| 4.4 | 6.0 | 0.22 | 1.28 | 1.37 | 1.01 | Yes | 67% |
| 4.5 | 8.0 | 0.17 | 1.33 | 1.37 | 1.01 | Yes | 74% |

(1) Total volume of samples 150 mL, pH 7
(2) Alco Aquatreat AR-4
(3) SNF Floquat 4540
(4) Stored at 49° C. for 2 days The data in Table 23 show that formulations with PECs and acceptable HOCl stability may be produced over a range of R values. Surprisingly, increasing the amount of poly(DADMAC) in the PECs, i.e., by increasing the R value, increases rather than decreases the stability of the HOCl.

Table 24 describes some compositions comprising PECs and HOCl as an oxidant in which the pH is adjusted to about neutral, pH 7.0

TABLE 24

Formulas containing HOCl with different succinate levels

| Sample # (1) | R | PAA mM | PDADMAC mM (3) | HOCl mM | Succinate mM | Phase Stable (4) | % HOCl remaining |
|---|---|---|---|---|---|---|---|
| 9.1 | 3.9 | 0.32 | 1.24 | 1.24 | 0.93 | Yes | 52% |
| 9.2 | 3.9 | 0.31 | 1.21 | 1.37 | 5.12 | Yes | 71% |
| 9.3 | 3.9 | 0.31 | 1.21 | 1.25 | 11.80 | Yes | 61% |

(1) Total volume of samples 150 mL, pH 7
(2) Alco Aquatreat AR-4
(3) SNF Floquat 4540
(4) Stored at 49° C. for 4 days The data in Table 24 show that PECs comprising PAA and poly(DADMAC) may be produced over a range of buffer (succinate) concentrations, i.e., the PECs are robust to a range of levels of ionic strength or electrolyte or, salt concentration which are useful in improving the stability of the HOCl oxidant.

Table 25 describes some compositions comprising PECs and HOCl as an oxidant in which the pH is adjusted to about neutral, i.e., pH 7.0

TABLE 25

Formulas containing HOCl with different PEC concentrations (low)

| Sample # (1) | R | PAA mM | PDADMAC mM (3) | Total Polymer mM | HOCl mM | Succinate mM | Phase Stable | % HOCl remaining |
|---|---|---|---|---|---|---|---|---|
| 4.1 | 3.9 | 1.53 | 6.00 | 7.53 | 1.33 | 5.01 | Yes | 12% |
| 4.2 | 3.9 | 0.31 | 1.21 | 1.52 | 1.33 | 5.01 | Yes | 77% |

TABLE 25-continued

Formulas containing HOCl with different PEC concentrations (low)

| Sample # (1) | R | PAA mM | PDADMAC mM (3) | Total Polymer mM | HOCl mM | Succinate mM | Phase Stable | % HOCl remaining |
|---|---|---|---|---|---|---|---|---|
| 4.3 | 4.0 | 0.06 | 0.24 | 0.30 | 1.33 | 5.01 | Yes | 89% |
| 4.4 | 3.9 | 0.01 | 0.05 | 0.06 | 1.33 | 5.01 | Yes | 91% |

(1) Total volume of samples 150 mL, pH 7
(2) Alco Aquatreat AR-4
(3) SNF Floquat 4540
(4) Stored at 49° C. for 2 days The data in Table 25 show that PECs comprising PAA and poly(DADMAC) can be produced with HOCl as an oxidant and that the stability of the HOCl can be adjusted by controlling the concentration of the PECs present, expressed as the total polymer concentration. Due to the high surface activity and adsorption of PECs onto surfaces, a wide range of PEC concentrations is found to be useful for producing hydrophilic modification of surfaces, improved wetting of HOCl solutions on hard surfaces, stain removal, and/or reduction of germs on surfaces.

Table 26 describes some compositions in which PECs were produced from various pairs of polyelectrolytes of opposite charge, at R values below and above 1.0, at pH adjusted to neutral, i.e., pH 7.0, in the presence of a buffer and HOCl as an oxidant.

TABLE 26

Formulas containing HOCl utilizing different polyelectrolytes

| Sample # (1) | R | A mM | B mM | C mM | D mM | E mM | F mM | Succinate mM | HOCl mM | Phase Stable (2) | % HOCl remaining (2) |
|---|---|---|---|---|---|---|---|---|---|---|---|
| 10.1 | 2.0 | 0.50 | — | — | 1.00 | — | — | 1.02 | 1.37 | Yes | 11% |
| 10.2 | 0.5 | — | 1.02 | — | 0.50 | — | — | 5.07 | 1.34 | Yes | 53% |
| 10.3 | 3.9 | — | 0.30 | — | 1.20 | — | — | 5.07 | 1.34 | Yes | 77% |
| 10.4 | 0.4 | — | — | 1.15 | 0.49 | — | — | 5.07 | 1.34 | Yes | 75% |
| 10.5 | 4.0 | — | — | 0.30 | 1.20 | — | — | 5.07 | 1.34 | Yes | 98% |
| 10.6 | 0.5 | — | 1.01 | — | — | 0.49 | — | 5.07 | 1.34 | Yes | 3% |
| 10.7 | 3.8 | — | 0.31 | — | — | 1.17 | — | 5.07 | 1.34 | Yes | 0% |
| 10.8 | 0.5 | — | 1.01 | — | — | — | 0.48 | 5.07 | 1.34 | Yes | 63% |
| 10.9 | 3.9 | — | 0.30 | — | — | — | 1.16 | 5.07 | 1.34 | Yes | 31% |

A = Polysytrene sulfonate, Alco Versa TL-70
B = Polyacrylic acid, Alco Aquatreat AR-4
C = Polyvinyl sulfate, Sigma-Aldrich #283215
D = Polydiallyl dimethyl ammonium chloride, SNF Floquat 4540
E = Poly(ethylenimine), Sigma-Aldrich #181978
F = Polyvinyl pyridine n-oxide, ISP Chromabond S-402E
(1) Total volume of samples 150 mL, pH 7
(2) Stored at 49° C. for 2 days The data in Table 26 indicate that formulations comprising stable PECs can be produced in solutions in which the pH is adjusted to neutral, i.e. pH 7.0, with a buffer suitable for use with HOCl as an oxidant. The compositions of the PECs can be varied over a wide range of R values, from significantly less than 1.0 to significantly greater than 1.0. Utilizing poly(DADMAC) as the polyelectrolyte bearing a cationic charge, stable PECs can be produced with a second polyelectrolyte bearing an anionic charge arising from a aromatic sulfonate-functional monomer (sample 10.1), a carboxylate-functional monomer (samples 10.2, 10.3), or a sulfate-functional monomer (samples 10.4, 10.5), with the latter two types of anionic polyelectrolytes being preferred for stability of HOCl at pH 7.0. Utilizing poly(ethyleneimine) as the polyelectrolyte capable of bearing a cationic charge, stable PECs can be produced with a second polyelectrolyte bearing an anionic charge arising from a carboxylate-functional monomer (samples 10.6, 10.7), although these PECs are not preferred in formulations containing HOCl near pH 7.0. Utilizing poly(vinyl pyridine) N-oxide as the polyelectrolyte capable of bearing a cationic charge, stable PECs can be produced with a second polyelectrolyte bearing an anionic charge arising from a carboxylate-functional monomer (samples 10.8, 10.9).

While particular embodiments of the present invention have been described with respect to compositions, methods of preparing compositions and methods of use, it will be clear that the invention is not limited to these illustrative embodiments only. Numerous modifications, changes, variations, substitutions and equivalents will be apparent to those skilled in the art without departing from the spirit and scope of the invention as described in the following claims.

We claim:

1. A treatment composition comprising:
   (i) water;
   (ii) at least one water-soluble associative polyelectrolyte complex formed by combining a water soluble cationic first polyelectrolyte; and a water soluble second polyelectrolyte bearing groups of opposite charge to said first polyelectrolyte; wherein the resulting water-soluble associative polyelectrolyte complex is non-precipitating in the treatment composition, wherein R, the molar ratio of charged groups present on said first polyelectrolyte to oppositely charged groups present on said second polyelectrolyte is from 0.10 to 20;

(iii) at least one buffer comprising at least one of: organic acids, mineral acids, alkali metal and alkaline earth salts of silicate, metasilicate, polysilicate, borate, carbonate, carbamate, citrate, phosphate, polyphosphate, pyrophosphates, triphosphates, tetraphosphates, ammonia, hydroxide, monoethanolamine, monopropanolamine, diethanolamine, dipropanolamine, triethanolamine, 2-amino-2methylpropanol, or mixtures thereof;

(iv) wherein said cationic first polyelectrolyte and said second polyelectrolyte each comprise at least one of homopolymers, random copolymers, alternating copolymers, or mixtures thereof;

(v) wherein neither said cationic first polyelectrolyte nor said second polyelectrolyte is a synthetic block copolymer;

(vi) wherein the at least one polyelectrolyte complex is at a concentration of no more than about 100 mM with respect to a total concentration of charged groups present on the first polyelectrolyte and the second polyelectrolyte making up the at least one polyelectrolyte complex;

(vii) wherein the at least one associative polyelectrolyte complex has an average aggregate size in solution of less than about 500 nanometers; and (viii) wherein film formation of the at least one water-soluble associative polyelectrolyte complex during use to treat a surface is self-limiting so as to not grow to macroscopic dimensions which would otherwise become visible to the eye, but instead maintaining a film thickness of less than about 500 nm.

2. The composition according to claim 1, wherein composition has a pH range of about 4-8.

3. The composition according to claim 1, wherein said cationic first polyelectrolyte comprises a cationic polymer with at least one monomer comprising at least one of: diallyl dimethyl ammonium salts, quaternary ammonium salts of substituted acrylamide, methacrylamide, acrylate and methacrylate, trimethyl-ammoniumethyl methacrylate, trimethylammoniumpropyl methacryl-amide, trimethylammonium methyl methacrylate, trimethylammonium-propyl acrylamide, 2-vinyl N-alkyl quaternary pyridinium, 4-vinyl N-alkyl quaternary pyridinium, 4-vinylbenzyltrialkylammonium, 2-vinyl piperidinium, 4-vinyl piperidinium, 3-alkyl 1-vinyl imidazolium, ionenes, acrylamide, N,N-dimethylacrylamide, N,N di-isopropyl-acryalmide, N-vinylimidazole, N-vinylpyrrolidone, vinyl pyridine N-oxide, ethyleneimine, dimethylamino-hydroxypropyl diethylenetriamine, dimethylaminoethyl methacrylate, dimethyl-aminopropyl methacrylamide, dimethylaminoethyl acrylate, dimethylaminopropyl acrylamide, 2-vinyl pyridine, 4-vinyl pyridine, 2-vinyl piperidine, 4-vinylpiperi-dine, vinyl amine, diallylamine, methyldiallylamine, vinyl oxazolidone; vinyl methyoxazolidone, and vinyl caprolactam, derivatives thereof, or combinations thereof.

4. The composition according to claim 1, wherein said water soluble second polyelectrolyte comprises an anionic polymer with a least one monomer comprising at least one of: acrylic acid, alginic acid, maleic acid, methacrylic acid, ethacrylic acid, dimethylacrylic acid, maleic anhydride, succinic anhydride, vinylsulfonate, cyanoacrylic acid, methylenemalonic acid, vinylacetic acid, allylacetic acid, ethylidineacetic acid, propylidineacetic acid, crotonic acid, fumaric acid, itaconic acid, sorbic acid, angelic acid, cinnamic acid, styrylacrylic acid, citraconic acid, glutaconic acid, aconitic acid, phenylacrylic acid, acryloxypropionic acid, citraconic acid, vinylbenzoic acid, N-vinylsuccinamidic acid, mesaconic acid, methacroylalanine, acryloylhydroxyglycine, sulfoethyl methacrylate, sulfopropyl acrylate, sulfoethyl acrylate, styrenesulfonic acid, acrylamide methyl propane sulfonic acid, 2-methacryloyloxymethane-1-sulfonic acid, 3-methacryloyloxypropane-1-sulfonic acid, 3-(vinyloxy)propane-1-sulfonic acid, ethylenesulfonic acid, vinyl sulfuric acid, 4-vinylphenyl sulfuric acid, ethylene phosphonic acid, vinyl phosphoric acid, derivatives therefore, or combinations thereof.

5. The composition according to claim 1, wherein said cationic first polyelectrolyte and said second polyelectrolyte are not selected from the group consisting of: polymer fluorosurfactant derived from polymerization of a fluorinated oxetane, cross-linked polyacrylic acid, a silicone polymer, anionic latex, water-insoluble anionic polysaccharide containing glucoronic acid, amphoteric derivatives of chitin or chitosan, including carboxymethyl N-acetyl chitosan, and a combination of chitosan and copolymers of acrylate and styrene monomers, and/or styrene derivatives, and combinations thereof.

6. The composition according to claim 1, wherein R is from 0.10 to 5.0.

7. An article of manufacture comprising a wipe, wherein the treatment composition of claim 1 is disposed on or within the wipe.

8. The composition according to claim 1, wherein the composition is optically clear.

9. A treatment composition comprising:
(i) water;
(ii) at least one water-soluble associative polyelectrolyte complex that is non-precipitating in the treatment composition, the at least one water-soluble associative polyelectrolyte complex being formed by combining:
   a. a water soluble cationic first polyelectrolyte comprising at least one monomer comprising at least one of: diallyl dimethyl ammonium salts, quaternary ammonium salts of substituted acrylamide, methacrylamide, acrylate and methacrylate, trimethyl-ammoniumethyl methacrylate, trimethylammoniumpropyl methacryl-amide, trimethylammonium methyl methacrylate, trimethylammonium-propyl acrylamide, 2-vinyl N-alkyl quaternary pyridinium, 4-vinyl N-alkyl quaternary pyridinium, 4-vinylbenzyltrialkylammonium, 2-vinyl piperidinium, 4-vinyl piperidinium, 3-alkyl 1-vinyl imidazolium, ionenes, and combinations thereof; and wherein said monomer capable of forming a cationic charge in solution upon protonation comprises at least one of acrylamide, N,N-dimethylacrylamide, N,N di-isopropyl-acryalmide, N-vinylimidazole, N-vinylpyrrolidone, vinyl pyridine N-oxide, ethyleneimine, dimethylamino-hydroxypropyl diethylenetriamine, dimethylaminoethyl methacrylate, dimethyl-aminopropyl methacrylamide, dimethylaminoethyl acrylate, dimethylaminopropyl acrylamide, 2-vinyl pyridine, 4-vinyl pyridine, 2-vinyl piperidine, 4-vinylpiperi-dine, vinyl amine, diallylamine, methyldiallylamine, vinyl oxazolidone; vinyl methyoxazolidone, and vinyl caprolactam, derivatives thereof, or combinations thereof; and
   b. a water soluble second polyelectrolyte bearing groups of opposite charge to said first polyelectrolyte comprising at least one monomer comprising at least one of: acrylic acid, alginic acid, maleic acid, methacrylic acid, ethacrylic acid, dimethylacrylic acid, maleic anhydride, succinic anhydride, vinylsulfonate, cyanoacrylic acid, methylenemalonic acid, vinylacetic acid, allylacetic acid, ethylidineacetic acid, propylidineacetic acid, crotonic acid, fumaric acid, itaconic acid, sorbic acid, angelic acid, cinnamic acid, styrylacrylic acid, citraconic acid, glutaconic acid, aconitic acid, phenylacrylic acid, acryloxypropionic acid, citraconic acid, vinylbenzoic acid, N-vinylsuccinamidic acid, mesaconic acid, methacroylalanine, acryloylhydroxyglycine, sulfoethyl methacrylate, sulfopropyl acrylate, sulfoethyl acrylate, styrenesulfonic acid, acrylamide methyl propane sulfonic acid, 2-methacryloyloxymethane-1-sulfonic acid, 3-methacryloyloxypropane-1-sulfonic acid, 3-(vinyloxy)propane-1-sulfonic acid, ethylenesulfonic acid, vinyl sulfuric acid, 4-vinylphenyl sulfuric acid, ethylene phosphonic acid, vinyl phosphoric acid, derivatives therefore, or combinations thereof;

wherein R, the molar ratio of charged groups present on said first polyelectrolyte to oppositely charged groups present on said second polyelectrolyte is from 0.10 to 20; and (iii) an antimicrobial agent comprising at least one of: alcohols, chlorinated hydrocarbons, organometallics, halogen-releasing compounds, metallic salts, pine oil, organic sulfur compounds, iodine compounds, antimicrobial metal cations and/or antimicrobial metal cation-releasing compounds, chitosan, quaternary ammonium compounds, phenolics, germicidal oxidants, germicidal essential oils, germicidal botanical extracts, alpha-hydroxycarboxylic acids, or combinations thereof;

(iv) wherein said cationic first polyelectrolyte and said second polyelectrolyte each comprise at least one of homopolymers, random copolymers, alternating copolymers, or mixtures thereof;

(v) wherein neither said cationic first polyelectrolyte nor said second polyelectrolyte is a synthetic block copolymer;

(vi) wherein the at least one polyelectrolyte complex is at a concentration of no more than about 100 mM with respect to a total concentration of charged groups present on the first polyelectrolyte and the second polyelectrolyte making up the at least one polyelectrolyte complex;

(vii) wherein the at least one associative polyelectrolyte complex has an average aggregate size in solution of less than about 500 nanometers; and (viii) wherein film formation of the at least one water-soluble associative polyelectrolyte complex during use to treat a surface is self-limiting so as to not grow to macroscopic dimensions which would otherwise become visible to the eye, but instead maintaining a film thickness of less than about 500 nm.

10. The composition according to claim 9, wherein the composition has a pH range of about 4-8.

11. The composition according to claim 9, wherein said composition further comprises at least one buffer comprising at least one of: organic acids, mineral acids, alkali metal and alkaline earth salts of silicate, metasilicate, polysilicate, borate, carbonate, carbamate, citrate, phosphate, polyphosphate, pyrophosphates, triphosphates, tetraphosphates, ammonia, hydroxide, monoethanolamine, monopropanolamine, diethanolamine, dipropanolamine, triethanolamine, and 2-amino-2methylpropanol, or mixtures thereof.

12. The composition according to claim 9, wherein R is from 0.20 to 3.0.

13. An article of manufacture comprising a wipe, wherein the treatment composition of claim 9 is disposed on or within the wipe.

14. The composition according to claim 9, wherein the composition is optically clear.

15. A treatment composition comprising:
(i) water;
(ii) at least one water-soluble associative polyelectrolyte complex that is non-precipitating in the treatment composition, the at least one water-soluble associative polyelectrolyte complex being formed by combining a water soluble cationic first polyelectrolyte; and a water soluble second polyelectrolyte bearing groups of opposite charge to said first polyelectrolyte; wherein R, the molar ratio of charged groups present on said first polyelectrolyte to oppositely charged groups present on said second polyelectrolyte is from 0.10 to 20;
(iii) an antimicrobial agent comprising at least one of: alcohols, chlorinated hydrocarbons, organometallics, halogen-releasing compounds, metallic salts, pine oil, organic sulfur compounds, iodine compounds, antimicrobial metal cations and/or antimicrobial metal cation-releasing compounds, chitosan, quaternary ammonium compounds, phenolics, germicidal oxidants, germicidal essential oils, germicidal botanical extracts, alpha-hydroxycarboxylic acids, or combinations thereof;
(iv) wherein said cationic first polyelectrolyte and said second polyelectrolyte each comprise at least one of homopolymers, random copolymers, alternating copolymers, or mixtures thereof;
(v) wherein neither said cationic first polyelectrolyte nor said second polyelectrolyte is a synthetic block copolymer;
(vi) wherein the at least one polyelectrolyte complex is at a concentration of no more than about 100 mM with respect to a total concentration of charged groups present on the first polyelectrolyte and the second polyelectrolyte making up the at least one polyelectrolyte complex;
(vii) wherein the at least one associative polyelectrolyte complex has an average aggregate size in solution of less than about 500 nanometers; and
(viii) wherein film formation of the at least one water-soluble associative polyelectrolyte complex during use to treat a surface is self-limiting so as to not grow to macroscopic dimensions which would otherwise become visible to the eye, but instead maintaining a film thickness of less than about 500 nm.

16. An article of manufacture comprising a wipe, wherein the treatment composition of claim 15 is disposed on or within the wipe.

17. The composition according to claim 15, wherein the composition is optically clear.

* * * * *